US008044179B2

(12) United States Patent
O'Connor-McCourt et al.

(10) Patent No.: US 8,044,179 B2
(45) Date of Patent: Oct. 25, 2011

(54) METHODS AND COMPOSITIONS FOR MODULATING TUMOR CELL ACTIVITY

(75) Inventors: Maureen D. O'Connor-McCourt, Beaconsfield (CA); Christiane Cantin, Pierrefonds (CA); Anne E. G. Lenferink, Lorraine (CA)

(73) Assignee: National Research Council of Canada

( * ) Notice: Subject to any disclaimer, the term of this patent is extended or adjusted under 35 U.S.C. 154(b) by 51 days.

(21) Appl. No.: 11/991,459

(22) PCT Filed: Sep. 13, 2006

(86) PCT No.: PCT/CA2006/001505
§ 371 (c)(1),
(2), (4) Date: Mar. 5, 2008

(87) PCT Pub. No.: WO2007/030930
PCT Pub. Date: Mar. 22, 2007

(65) Prior Publication Data
US 2009/0104215 A1 Apr. 23, 2009

Related U.S. Application Data

(60) Provisional application No. 60/716,086, filed on Sep. 13, 2005.

(51) Int. Cl.
C07K 16/00 (2006.01)
A61K 39/395 (2006.01)
A61K 39/00 (2006.01)

(52) U.S. Cl. .............. 530/387.1; 530/388.1; 424/130.1; 424/141.1

(58) Field of Classification Search .................. None
See application file for complete search history.

(56) References Cited

U.S. PATENT DOCUMENTS

| | | |
|---|---|---|
| 6,383,808 B1 | 5/2002 | Freier |
| 6,464,975 B2 | 9/2002 | Millis |
| 6,900,187 B2 | 9/2003 | Gleave |
| 7,279,294 B2 | 11/2003 | Morin |
| 7,285,541 B2 | 4/2004 | Gleave |
| 6,812,339 B1 | 11/2004 | Venter |
| 7,691,382 B2 | 5/2007 | Dobson |
| 7,309,487 B2 | 12/2007 | Inana |
| 7,597,888 B2 | 2/2008 | Gill |
| 7,585,937 B2 | 5/2008 | Kungl |
| 2003/0134301 A1 | 7/2003 | Brooksbank et al. |
| 2003/0162702 A1 | 8/2003 | Millis |
| 2003/0211476 A1 | 11/2003 | O'Mahony |
| 2004/0082534 A1 | 4/2004 | Gleave |
| 2004/0220131 A1 | 11/2004 | Jackson |
| 2004/0224914 A1 | 11/2004 | Jackson |
| 2005/0048490 A1 | 3/2005 | Azimzai |
| 2005/0152903 A1 | 7/2005 | Newman |
| 2005/0222027 A1 | 10/2005 | Chiang |
| 2005/0255114 A1 | 11/2005 | Labat |
| 2006/0029956 A1 | 2/2006 | Beyer |
| 2006/0088532 A1 | 4/2006 | Helsinki et al. |
| 2006/0122141 A1 | 6/2006 | Gleave |
| 2006/0251668 A1 | 11/2006 | Goletz |
| 2007/0015145 A1 | 1/2007 | Woolf |
| 2007/0042945 A1 | 2/2007 | Bodary |
| 2007/0082337 A1 | 4/2007 | Sorek |
| 2007/0083334 A1 | 4/2007 | Mintz |
| 2007/0099242 A1 | 5/2007 | Heinecke |
| 2007/0105114 A1 | 5/2007 | Li |
| 2007/0117746 A1 | 5/2007 | Dobson |
| 2007/0134260 A1 | 6/2007 | Feger |
| 2007/0224201 A1 | 9/2007 | Wu |
| 2008/0014198 A1 | 1/2008 | Gleave |
| 2008/0064651 A1 | 3/2008 | Gleave |
| 2008/0070995 A1 | 3/2008 | Westbrook |
| 2008/0119425 A1 | 5/2008 | Gleave |
| 2008/0253963 A1 | 10/2008 | Morin |
| 2008/0261912 A1 | 10/2008 | Gleave |
| 2008/0274996 A1 | 11/2008 | Gleave |
| 2008/0286834 A1 | 11/2008 | Halenbeck |
| 2008/0293070 A1 | 11/2008 | Sekaly |
| 2008/0307537 A1 | 12/2008 | Bachoo |
| 2008/0317771 A1 | 12/2008 | Spagnoli |
| 2009/0005541 A1 | 1/2009 | Kungl |
| 2009/0018026 A1 | 1/2009 | Kim |
| 2009/0048171 A1 | 2/2009 | Dobson |
| 2009/0053828 A1 | 2/2009 | Regnier |
| 2009/0081685 A1 | 3/2009 | Beyer |
| 2009/0117578 A1 | 5/2009 | Metz |
| 2009/0144839 A1 | 6/2009 | Inana |
| 2009/0181380 A1 | 7/2009 | Belouchi |

(Continued)

FOREIGN PATENT DOCUMENTS

EP 1358326 9/2002

(Continued)

OTHER PUBLICATIONS

Rudikoff, Giusti, Cook, and Scharff. Single amino acid substitution altering antigen-binding specificity. Proceedings of the National Academy of Sciences, 1982. vol. 79, pp. 1979-1983.*

Mac Callum, Martin and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

(Continued)

Primary Examiner — Anne M. Gussow
(74) Attorney, Agent, or Firm — Janique Forget

(57) ABSTRACT

Antibodies which target clusterin, a protein involved in the epithelial-to-mesenchymal transition of carcinoma cells, are identified and characterized. The antibodies may be used to modulate tumour cell activity through binding to clusterin.

29 Claims, 36 Drawing Sheets

U.S. PATENT DOCUMENTS

| | | | |
|---|---|---|---|
| 2009/0203639 | A1 | 8/2009 | Van Criekinge |
| 2009/0208921 | A1 | 8/2009 | Tempst |
| 2009/0215709 | A1 | 8/2009 | Van Criekinge |
| 2009/0238832 | A1 | 9/2009 | Bodary-Winter |
| 2009/0258089 | A1 | 10/2009 | Gleave |
| 2009/0280124 | A1 | 11/2009 | Labat |
| 2009/0292008 | A1 | 11/2009 | Gleave |
| 2010/0075866 | A1 | 3/2010 | Hood |
| 2010/0086541 | A1 | 4/2010 | Wu |

FOREIGN PATENT DOCUMENTS

| | | |
|---|---|---|
| EP | 1603514 | 8/2004 |
| EP | 2008100 | 1/2007 |
| EP | 1716227 | 4/2007 |
| EP | 2057465 | 2/2008 |
| EP | 2087152 | 5/2008 |
| EP | 1940457 | 7/2008 |
| EP | 2014675 | 1/2009 |
| JP | 2004521627 | 9/2002 |
| JP | 2004513626 | 5/2007 |
| JP | 2007535910 | 5/2007 |
| JP | 2008506123 | 2/2008 |
| WO | WO 91/05043 | 4/1991 |
| WO | WO9105043 | 4/1991 |
| WO | WO 00/34469 | 6/2000 |
| WO | WO0166689 | 9/2001 |
| WO | WO02072830 | 9/2002 |
| WO | WO03016475 | 2/2003 |
| WO | WO03054152 | 7/2003 |
| WO | WO2004005934 | 1/2004 |
| WO | WO2004050707 | 6/2004 |
| WO | WO2004066941 | 8/2004 |
| WO | WO2005016962 | 2/2005 |
| WO | WO2005049806 | 6/2005 |
| WO | WO2005060457 | 7/2005 |
| WO | WO 2005/080434 A1 | 9/2005 |
| WO | WO2005080434 | 9/2005 |
| WO | WO2006035237 | 4/2006 |
| WO | WO2006081430 | 8/2006 |
| WO | WO2006089586 | 8/2006 |
| WO | WO2006113671 | 10/2006 |
| WO | PCT/CA2006/001505 | 12/2006 |
| WO | WO2007047995 | 4/2007 |
| WO | WO2007123976 | 11/2007 |
| WO | WO2008021290 | 2/2008 |
| WO | WO2008049239 | 5/2008 |
| WO | WO2008085035 | 7/2008 |
| WO | WO2008104808 | 9/2008 |
| WO | WO2009034562 | 3/2009 |
| WO | WO2009061382 | 5/2009 |
| WO | WO2009090553 | 7/2009 |
| WO | WO2009093246 | 7/2009 |
| WO | WO2009116860 | 9/2009 |

OTHER PUBLICATIONS

Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Paul. Fundamental Immunology, 3$^{rd}$ Edition, 1993. pp. 292-295.*

Colman. Research in Immunology, 1994. vol. 145, pp. 33-36.*

Miyake H. et al., Acquisition of Chemoresistant Phenotype by Overexpression . . . , Cancer Research 60, pp. 2547-2554, May 1, 2000.

So Alan et al., Antisense Oligonucloetide Therapy in the Managment of Bladder Cancer, Curr. Opin. Urol. 15, pp. 320-327, (2005).

Zellweger T. et al., Antitumor Activity of Antisense Clusterin Oligonucleotides . . . , The J. of Pharmacology and Experimental Therapeutics, 298, pp. 934-940 (2001).

Miyake H. et al., Introducing the Clusterin Gene Into Human Renal Cell Carninoma . . . , The Journal of Urology, 167 pp. 2203-2208 May 2002.

So A. et al., Knockdown of the Cytoprotective Chaperone, Clusterin, Chemosensitizes Human Breast Cancer Cells . . . Mol. Cancer Ther. 4 (12), pp. 1837-1849, Dec. 2005.

Park Dong C. et al., Clusterin Interacts with Paclitaxel and Confer Paclitaxel Resistance in Ovarian Cancer, Neoplasia Press, vol. 10, pp. 964-972, Sep. 2008.

Miyake H. et al., Overexpression of Clusterin in Transitional Cell Carcinoma of the Bladder . . . , Urology, 59, pp. 150-154 Elsevier Science (2002).

Hara I. et al., Introduction of Clusterin Gene into Human Renal Cell Carcinoma Cells Enhances, Jpn. J. Cancer Res. 92, pp. 1220-1224, Nov. 2001.

Kurisaki et al.; Nuclear factor YY1 inhibits transforming growth factor beta- and bone morphogenetic protein-induced cell differentiation; Mol Cell Biol. (2003) 23:4494-510.

Li et al.; Predicting Protein Disorder for N-, C-, and Internal Regions. Genome Informatics (1999); 10: 30-40.

GenBank accession No. AAA30846, Hartmann, K. et al. J. Biol. Chem. 266 (15), pp. 9924-9931 (1991).

GenBank accession No. AAA31013, Diemer, V. J. Biol. Chem. 267 (8), pp. 5257-5264 (1992).

GenBank accession No. AAA35692, Jenne, D.E. and Tschopp, J. Journal Proc. Natl. Acad. Sci. U.S.A. 86 (18), pp. 7123-7127 (1989).

GenBank accession No. AAA37284, Hodgdon, B. A. et al. "Secretion of sulfated glycoprotein . . . " Apr. 27, 1993.

GenBank accession No. AAA37422, French, L.E. et al., J. Cell biol. 122 (5), pp. 1119-1130 (1993).

GenBank accession No. AAA41273, Collard, M. W. and Griswold, M. D. J. Biochemistry 26 (12), pp. 3297-3303 (1987).

GenBank accession No. AAA42298, Wong, P. et al. J. Biol. Chem. 268 (7), pp. 5021-5031 (1993).

GenBank accession No. AAA42299, Wong, P. et al. J. Biol. Chem. 268 (7), pp. 5021-5031 (1993).

GenBank accession No. AAA51765, de Silva, H.V. et al., J. Biochemistry 29 (22), pp. 5380-5389 (1990).

GenBank accession No. AAA60321, Danik, M. et al. J. Proc. Natl. Acad. Sci. U.S.A. 88 (19), pp. 8577-8581 (1991).

GenBank accession No. AAA60567, Glew, M.D. et al. Partial mucleotide sequence of the human SP40, 40 gene Jan. 13, 1995.

GenBank accession No. AAA80313, Barber, J. A. et al., "Nucleotide sequence of the complementary DNA . . . " Nov. 1, 1995.

GenBank accession No. AAB06507, Wong P. et al. Eu. J. Biochem. 221 (3), 917-925 (1994).

GenBank accession No. AAB06508, Wong, P. et al. Eur. J. Biochem. 221 (3) pp. 917-925 (1994).

GenBank accession No. AAB25217, Choi-Miura, N.H. et al. J. Biochem. 112 (4), pp. 557-561 (1992).

GenBank accession No. AAB30623, Jordan-Starck, T.C. et al. J. Lipid Res. 35 (2), pp. 194-210 (1994).

GenBank accession No. AAD24461, Miyata, M. et al., Direct submission, Submitted Jan. 8, 1999, First Deaprtment of Internal Medecine, Kagoshima University.

GenBank accession No. AAF06365, Jordan-Starck, T.C. et al., Direct Submission, submittted Sep. 2, 1999, Molecular Developmental Biology.

GenBank accession No. AAF67184, You K.H. and Jeon J.H. Direct Submission, submitted Mar. 22, 2000, Department of Biology, Chungnam National University.

GenBank accession No. AAF67185, You K.H. and Jeon J.H. Direct Submission, submitted Mar. 22, 2000, Department of Biology, Chungnam National University.

GenBank accession No. AAG31162,Park, J. H. et al. Direct Submission Submitted Oct. 19, 2000 Protein Eng. Laboratory, Korea Res. Inst. of Bioscience and Biotechnology.

GenBank accession No. AAH10514, Strausberg R.L. et al., J. Proc. natl. Acad. Sci. U.S.A. 99 (26), pp. 16899-16903 (2002).

GenBank accession No. AAH19588, Strausberg R.L. et al., J. Proc. natl. Acad. Sci. U.S.A. 99 (26), pp. 16899-16903 (2002).
GenBank accession No. AAH61534, Strausberg R.L. et al., J. Proc. natl. Acad. Sci. U.S.A. 99 (26), pp. 16899-16903 (2002).
GenBank accession No. AAH75668, Strausberg, R. L. et al. J., Direct Submission, Proc. Natl. Acad. Sci. U.S.A. 99 (26), pp. 16899-16903 (2002), NIH MGC Project, Jun. 29, 2004.
GenBank accession No. AAP88927, Rieder, M.J. et al., Direct Submission, Submitted Jul. 11, 2003, Genome Sc., University of Washigton.
GenBank accession No. AAT08041, Kim, J.W., Direct Submission, Submitted Dec. 26,2003, J. Obstet. & Gynecol.Catholic University Medical College.
GenBank accession No. AAV67360-Dorus, S. et al. Direct Submission, Department of Human Genetics, Medical Institute, University of Chicago, Submitted Jun. 14, 2004.
GenBank accession No. AAX36279-Hines, L. et al, Biological Chemistry and Molecular Pharmacology, Harvard Institute of Proteomics, submitted Jan. 4, 2005.
GenBank accession No. AAX41112-Hines, L. et al. Direct Submission, Biol. Chem. and Mol. Pharmacology, Harvard Institute of Proteomics, submitted Jan. 4, 2005.
GenBank accession No. AAX42684-Hines, L. et al. "Direct Submission" Biol.Chem. and Mol. Phar., Harvard Inst. of Proteomics, submitted Jan. 5, 2005.
GenBank accession No. ABM82371, Rolfs, A. et al., Direct Submission, submitted Jan. 22, 2007.
GenBank accession No. ABM85549, Rolfs, A. et al., Direct Submission, submitted Jan. 22, 2007.
GenBank accession No. BAA03162, You, K. -H. Direct Submission, Submitted Jan. 18, 1993.
GenBank accession No. BAE88332, Chien, H. -C. et al. Direct Submission, submitted Mar. 19, 2004.
GenBank accession No. BAE88970, Chien, H. -C. et al. Direct Submission, submitted Mar. 19, 2004.
GenBank accession No. BAG36598, Isogai, T. And Yamamoto J., Direct Submission, submitted Jan 11, 2008.
GenBank accession No. BAG52708, Isogai, T. and Yamamoto, J., Direct Submission, submitted Jul. 4, 2002, Helix Research Institute, Genomics Laboratory.
GenBank accession No. CAA31618, Bettuzzi, S., Direct Submission, submitted Oct. 11, 1988) Ben May Institute, University of Chicago.
GenBank accession No. CAA32847, Kirszbaum, L., Direct Submission, submitted Mar. 17, 1999, Clin. Invest. 81, pp. 1858-1864 (1988).
GenBank accession No. CAI45990, Bloecker H. et al., Direct Submission, submitted Jan. 20, 2005, MIPS, Ingolstaedter Landstr. 1.
UniProtKB/Swiss-Prot accession No. P25473 (CLUS_CANFA), Hartmann K. et al., J. Biol. Chem, 266:9924-9931 (1991) May 1, 1992.
UniProtKB/Swiss-Prot accession No. Q29482 (CLUS_HORSE), Barber J. A. et al., submitted Nov. 1995, May 10, 2005.
UniProtKB/Swiss-Prot accession No. P10909 (CLUS_HUMAN), Jenne D.E. and Tschopp J., Proc. natl. Acad. Sci. U.S.A. 86:7123-7127 (1989), Jul. 1, 1989.
UniProtKB/Swiss-Prot accession No. Q06890 (CLUS_MOUSE), Lee K.-H. et al. Biochem. Biophys. Res. Commun. 194:1175-1180 (1993) PubMed: 8352774 Abstract, Feb. 1, 1995.
UniProtKB/Swiss-Prot accession No. Q29549 (CLUS_PIG), Diemer V. et al., J. Biol. Chem. 267:5257-5264 (1992), Jul. 15, 1998.
UniProtKB/Swiss-Prot accession No. Q9XSC5 (CLUS_RABIT), Miyata M. et al., Circulation 104:1407-1412 (2001) Dec. 1, 2000.
NCBI Reference sequence: NP_038520, Jenne, D.E. and Tschopp, J. Proc. natl. Acad. Sci. U.S.A. 86 (18), pp. 7123-7127 (1989).
NCBI Reference sequence: NP_444180, Collard, M. W. and Griswold, M. D., Biochemistry 26 (12) pp. 3297-3303 (1987).
NCBI Reference sequence:NP_976084, James, R. W. et al. Arterioscler. Thromb. 11 (3), pp. 645-652 (1991).
NCBI Reference sequence: NP_999136, Diemer, V. et al. J. Biol. Chem. 267 (8), pp. 5257-5264 (1992).
Uni-Prot/TrEMBL accession No. Q549A5_MOUSE, McLaughlin L. et al., J. Clin. Invest. 106:1105-1113 (2000) May 24, 2005.

Uni-Prot/TrEMBL accession No. Q5ISQ2_MACFA, Dorus S. et al., Cell 119:1027-1040 (2004).
Uni-Prot/TrEMBL accession No. Q6P7S6_RAT, Jul. 5, 2004.
Uni-Prot/TrEMBL accession No. Q9ERD1_RAT, Park J. H. et al., submitted Oct. 2000, Mar. 1, 2001.
NCBI Reference sequence: XP_001164036, Sep. 15, 2006.
NCBI Reference sequence: XP_001164195, Sep. 15, 2006.
NCBI Reference sequence: XP_001164234, Sep. 15, 2006.
NCBI Reference sequence: XP_001164274, Sep. 15, 2006.
NCBI Reference sequence: XP_001164305, Sep. 15, 2006.
NCBI Reference sequence: XP_001164341, Sep. 15, 2006.
NCBI Reference sequence: XP_001164378, Sep. 15, 2006.
NCBI Reference sequence: XP_001164413, Sep. 15, 2006.
NCBI Reference sequence: XP_001164451, Sep. 15, 2006.
NCBI Reference sequence: XP_001164491, Sep. 15, 2006.
NCBI Reference sequence: XP_001164530, Sep. 15, 2006.
NCBI Reference sequence: XP_001164568, Sep. 15, 2006.
NCBI Reference sequence: XP_001164607 Sep. 15, 2006.
NCBI Reference sequence: XP_001164647 Sep. 15, 2006.
NCBI Reference sequence: XP_001475661 Jun. 20, 2007.
NCBI Reference sequence: XP_519677 Sep. 15, 2006.
July L.V. et al., "Clusterin expression is significantly enhanced in prostate cancer cells following androgen . . . " Prostate, vol. 50, No. 3, Feb. 15, 2002, pp. 179-188.
Cerverella M. et al. "Direct transactivation of the anti-apoptotic gene apolipoprotein J (clusterin) . . . " The J. of Biol.Chemistry, vol. 275, No. 28, Jul. 14, 2000 pp. 21055-21066.
Santa Cruz Biotechnology Inc. "Clustrein-alpha (C-18); sc-6429" Santa Cruz Biotechnology Inc. Catalog. 1999, p. 1.
Santa Cruz Biotechnology Inc. "Clustrein-alpha (B-5); sc-5289" Santa Cruz Biotechnology Inc. Catalog. 2004 p. 1.
Chou Teh-Ying et al., "Clusterin silencing in human lung adenocarcinoma cells induces a mesenchymal-to-epithelial . . . " Cell, signaling 2009. vol. 21, No. 5, May 2009,pp. 704-771.
Krüger S, et al., "Value of clusterin immunoreactivity as a predictive factor in muscle-invasive urothelial bladder carcinoma." Urology. Jan. 2006;67(1):105-9.
Kurahashi T, et al., "Expression of the secreted form of clusterin protein in renal cell carcinoma as a predictor of disease extension." BJU Int. Oct. 2005;96(6):895-9.
Chung J, et al. "Enhanced chemosensitivity of bladder cancer cells to cisplatin by suppression of clusterin in vitro."Cancer Lett. Jan. 20, 2004;203(2)155-61.
Scaltriti M, et al., "Clusterin (SGP-2, ApoJ) expression is downregulated in low- and high-grade human prostate cancer." Int J Cancer. Jan. 1, 2004;108(1):23-30.
Zhang LY, et al., "Loss of clusterin both in serum and tissue correlates with the tumorigenesis of esophageal squamous cell carcinoma . . . " World J Gastro. Apr. 2003;9(4):650-4.
Lee CH, et al., "Suppression of clusterin expression enhanced cisplatin-induced cytotoxicity on renal cell carcinoma cells." Urology. Sep. 2002;60(3):516-20.
Gleave ME, et al., "Targeting anti-apoptotic genes upregulated by androgen withdrawal using antisense oligonucleotides to . . . " Invest New Drugs. May 2002;20(2):145-58.
Miyake H, et al., "Introducing the clusterin gene into human renal cell carcinoma cells enhances their metastatic potential." J Urol. May 2002;167(5):2203-8.
Deng HB, et al., "Increased expression of dihydrodiol dehydrogenase induces resistance to cisplatin in human . . . " J Biol Chem. Apr. 26, 2002;277(17):15035-43. Epub Feb. 12, 2002.
Chi Kim N. et al., "A phase I pharmacokinetic and pharmacodynamic study of OGX-011, a 2'-methoxyethyl . . . " J. of the Nat. Cancer Inst. Sep. 7, 2005, vol. 97 No. 17, pp. 1287-1296.
Lau SH, et al., "Clusterin plays an important role in hepatocellular carcinoma metastasis." Oncogene. Feb. 23, 2006;25 (8):1242-50.
Park DC, et al. "Clusterin confers paclitaxel resistance in cervical cancer." Gynecol Oncol. Dec. 2006;103(3):996-1000. Epub Aug. 4, 2006.
Xie D, et al., "Oncogenic role of clusterin overexpression in multistage colorectal tumorigenesis and progression." World J Gastroenterol. Jun. 7, 2005;11(21):3285-9.

Kang YK, "Overexpression of clusterin in human hepatocellular carcinoma." Hum Pathol. Nov. 2004;35(11):1340-6.
Xie D, et al. "Up-regulated expression of cytoplasmic clusterin in human ovarian carcinoma."Cancer. Jan. 15, 2005;103(2):277-83.
Springate CM, et al., "Efficacy of an intratumoral controlled release formulation of clusterin antisense . . . " Cancer Chemother Pharmacol. Sep. 2005;56(3):239-47. Epub Apr. 3, 2005.
UniProtKB/Swiss-Prot accession No. P05371 (CLUS_RAT), Collard M.W. and Grisworld M.D., Biochemistry 26:3297-3303 (1987).
IPI No: IPI00198667.7, Mar. 14, 2003.
IPI No: IPI00291262.3, Jun. 6, 2003.
IPI No: IPI00320420.3, Jun. 11, 2003.
IPI No: IPI00400826.1, Mar. 3, 2004.
IPI No:IPI00753742.1, May 10, 2006.
IPI No: IPI00795633.1, Oct. 31, 2006.
NCBI Reference sequence: NP_001003370, Hartmann, K. et al., J. Biol. Chem. 266 (15) pp. 9924-9931 (1991).
NCBI Reference sequence: NP_001075413, Sep. 3, 2009.
NCBI Reference sequence: NP_001075518, Miyata, M., Circulation 104 (12) pp. 1407-1412 (2001).
NCBI Reference sequence: NP_001822, James, R. W. et al. Arterioscler. Thromb. 11 (3) pp. 645-652 (1991).
Zellweger T, et al., "Chemosensitization of human renal cell cancer using antisense oligonucleotides targeting the antiapoptotic gene . . . " Neoplasia. Jul.-Aug. 2001;3(4):360-7.
Redondo M, et al., "Overexpression of clusterin in human breast carcinoma." Am J Pathol. Aug. 2000;157(2):393-9.
Steinberg J, et al., "Intracellular levels of SGP-2 (Clusterin) correlate with tumor grade in prostate cancer." Clin Cancer Res. Oct. 1997;3(10):1707-11.
Parczyk K, et al., "GpBO (clusterin; TRPM-2) mRNA level is enhanced in human renal clear cell carcinomas." J Cancer Res Clin Oncol. 1994;120(3):186-8.
July LV, et al.,"Nucleotide-based therapies targeting clusterin chemosensitize human lung adenocarcinoma cells both in vitro and in vivo." Mol Cancer Ther.Mar. 2004;3(3):223-32.
He HZ, et al., "Alterations in expression, proteolysis and intracellular localizations of clusterin in esophageal squamous cell . . . " W. J Gastro. May 15, 2004;10(10):1387-91.
Thomas-Tikhonenko A, et al., "Myc-transformed epithelial cells down-regulate clusterin, which inhibits their growth in vitro and . . . " Cancer Res. May 1, 2004;64(9):3126-36.
Bailey, R.W., et al., Clusterin, a Binding Protein with a Molten Globule-like Region; Biochemistry; (2001), 40(39):11828-11840, American Chemical Society, USA.
Zhou Wei et al. A novel anti-proliferative property of Clusterin in prostate cancer cells. Life Sciences, (Nov. 22, 2002), 72(1):11-21.
Lenferink, A.E.G. et al., Investigation of three new mouse mammary tumor cell lines as models for transforming growth factor (TGF)-beta and Neu pathway signaling studies: identification of a novel model for TGF-beta-induced epithelial to mesenchymal transition. Breast Cancer Res. (2004), 6:R514-R530.
Lenferink A.E.G. et al., Transcriptome profiling of a TGF-beta-induced epithelial-to-mesenchymal transition reveals extracellular clusterin as a target for therapeutic antibodies, Oncogene(Feb. 11, 2010);29(6):831-44. Epub Nov. 23, 2009.
Trougakos, I.P. et al., Advances and Challenges in Basic and Translational Research on Clusterin. Cancer Res. (2009); 69(2):403-406 including 4 pages of "Supplementary data".
Abdellattif, E. et al. Identification of Clusterin domain involved in NF-kappaB pathway regulation. Journal of Biological Chemistry(2010) 285:4273-4277. Epub Dec. 22, 2009.
Ensembl Protein ID: ENSCAFP00000012350: Jun. 8, 2010.
Ensembl Protein ID:ENSCAFP00000034804: Jun. 8, 2010.
Ensembl Protein ID:ENSECAP00000005450: Jun. 8, 2010.
Ensembl Protein ID:ENSEEUP00000006956: Jun. 8, 2010.
Ensembl Protein ID:ENSFCAP00000013377: Jun. 8, 2010.
Ensembl Protein ID:ENSMICP00000007021: Jun. 8, 2010.
Ensembl Protein ID:ENSMLUP00000006142: Jun. 8, 2010.
Ensembl Protein ID:ENSMMUP00000032168: Jun. 8, 2010.
Ensembl Protein ID:ENSMMUP00000032169:Jun. 8, 2010.
Ensembl Protein ID:ENSMMUP0000028339: Jun. 8, 2010.
Ensembl Protein ID:ENSMMUP0000032167: Jun. 8, 2010.
Ensembl Protein ID:ENSMMUP0000032170: Jun. 8, 2010.
Ensembl Protein ID:ENSMUSP00000022616: Jun. 8, 2010.
Ensembl Protein ID:ENSOCUP00000005178: Jun. 8, 2010.
Ensembl Protein ID:ENSOPRP00000000527: Jun. 8, 2010.
Ensembl Protein ID:ENSPPYP00000020696: Jun. 8, 2010.
Ensembl Protein ID:ENSPTRP00000034423: Jun. 8, 2010.
Ensembl Protein ID:ENSPTRP00000056651: Jun. 8, 2010.
Ensembl Protein ID:ENSRNOP00000022095: Jun. 8, 2010.
Staelens: Humanization by variable domain resurfacing and grafting on a human lgG4, using a new approach for determination of non human like surface accessible framework residues based on homology modelling of variable domains. EMBL-EBI (Jun. 20, 2005) acces.No. AJ965435.
Van Der Keyl: Mus musculus anti-fluorescein lg light chain mRNA. EMBL-EBI (Aig. 9, 1999) acces.No. AF139227.
ISR and Written Opinion, Dec. 27, 2006.
Al Moustafa, et al. Black Cellular Spreading and Motility Assay; BioTechniques, (Jul. 1999), 27:60-62.
Bailey, et al. Clusterin, a Binding Protein with a Molten Globule-like Region; BioTechniques, 2001, 40:11828-11840, American Chemical Society USA.
Dunker, Intrinsically Disordered Protein; Journal of Molecular Graphics and Modelling 2001,19:26-59, Elsevier Science Inc. NY.
Durocher, Yves; High-level and high-throughput recombinant protein production by transient transfection of suspension-growing human 293-EBNA1 cells; Nucleic Acids Research, 2002,30:1-9, Oxford University Press England.
Enjalbert, Stress-Induced Gene Expression in Candida albicans: Absence of a General Stress Response; Molecular Biology of the Cell; (Apr. 2003), 14:1460-1467.
Wilson, Clusterin Binds by a Multivalent Mechanism to the Fc and Fab regions of IgG; Biochimica et BiophysicaActa; 1992, 1159:319-326, Elsevier Science Publishers B.V.
Jones, GenTHREADER: An Efficient and Reliable Protein Fold Recognition Method for Genomic Sequences, J.Mol.Biol.1999,287:797-815, http://www.idealibrary.com.
Lupas, Prediction and Analysis of Coiled-Coil Structures, Methods in Enzymology, 1996,266:513-524, Academic Press, Inc.
Rost, PHD: Predicting One-Dimensional Protein Structure by Profile-Based Neural Networks, Methods in Enzymology, 1996, 266:525-539.
Schade et al, Cold Adaptation in Budding Yeast, Molecular Biology of the Cell, 2004, 15:5492-5502.
Singh, Transforming the TGFβ pathway: Convergence of distinct lead generation strategies on a novel kinase pharmacophore for TβRI (ALK5), Curr.Opin Drug Discov Devel. 2004 74:437-445.
He et al, Alterations in expression, proteolysis and intracellular localizations of clusterin in esophageal squamous cell carcinoma,World J. Gastroenterol, 2004, 10(1):1387-1391.
Miyake, Hideaki et al. Resistance to cytotoxic chemotherapy-induced apoptosis in human prostate cancer cells is associated with intracellular clusterin expression, Oncology Reports, 2003, 10:469-473.
Sintich et al, Transforming Growth Factor-β1-Induced Proliferation of the Prostate Cancer Cell Line, TSU-Pr1: The Role of Platelet-Derived Growth Factor, Endocrinology, 1999, 140:3411-3415.
Sintich, Cytotoxic Sensitivity to Tumor Necrosis Factor-α in PC3 and LNCaP Prostatic Cancer Cells Is Regulated by Extracellular Levels of SGP-2 (Clusterin), The Prostate 1999, 39:87-93.
Trougakos, Ioannis, Differential effects of clusterin/apolipoprotein J on cellular growth and survival.Free Radical Biology & Medicine 2005, 38:436-449.
Lenferink, Clusterin Mediates Tumor Promoting, But Not Tumor Suppressing, Effects of TGF-β1, National Research Council of Canada May 2004, Poster at NRC AGM, 2.

* cited by examiner

Annexin
Basic fibroblast growth factor receptor
Cathepsin L
Clusterin
CSF-1
Fibronectin
Four-and-a-half LIM domains
Integrin β1
Laminin
Platelet derived growth factor-A
Serum/glucocorticoid regulated kinase
Syndecan 1 and 3
Ras homolog B
Tumor associated antigen L6
Urokinase plasminogen activator receptor

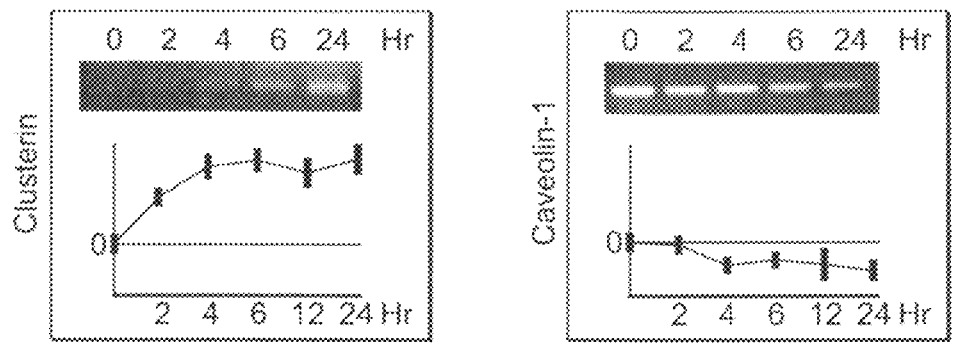
FIG. 3A
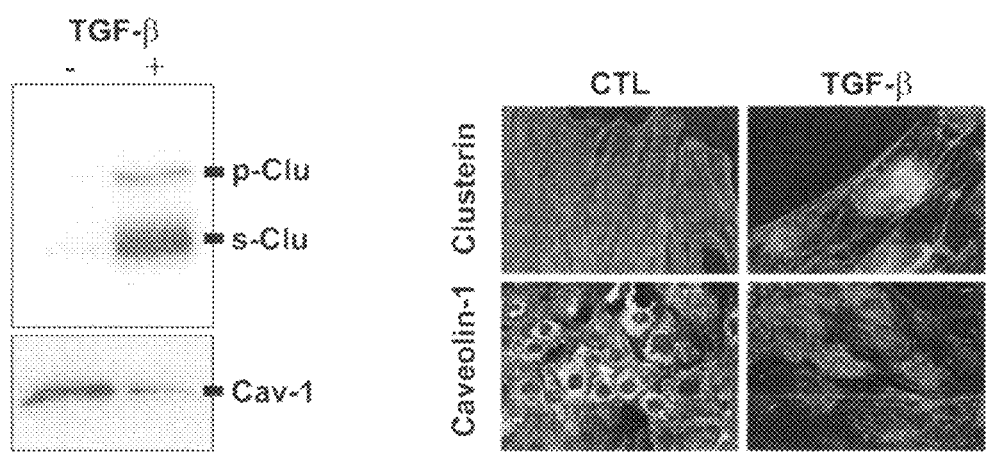
FIG. 3B
FIG. 3C

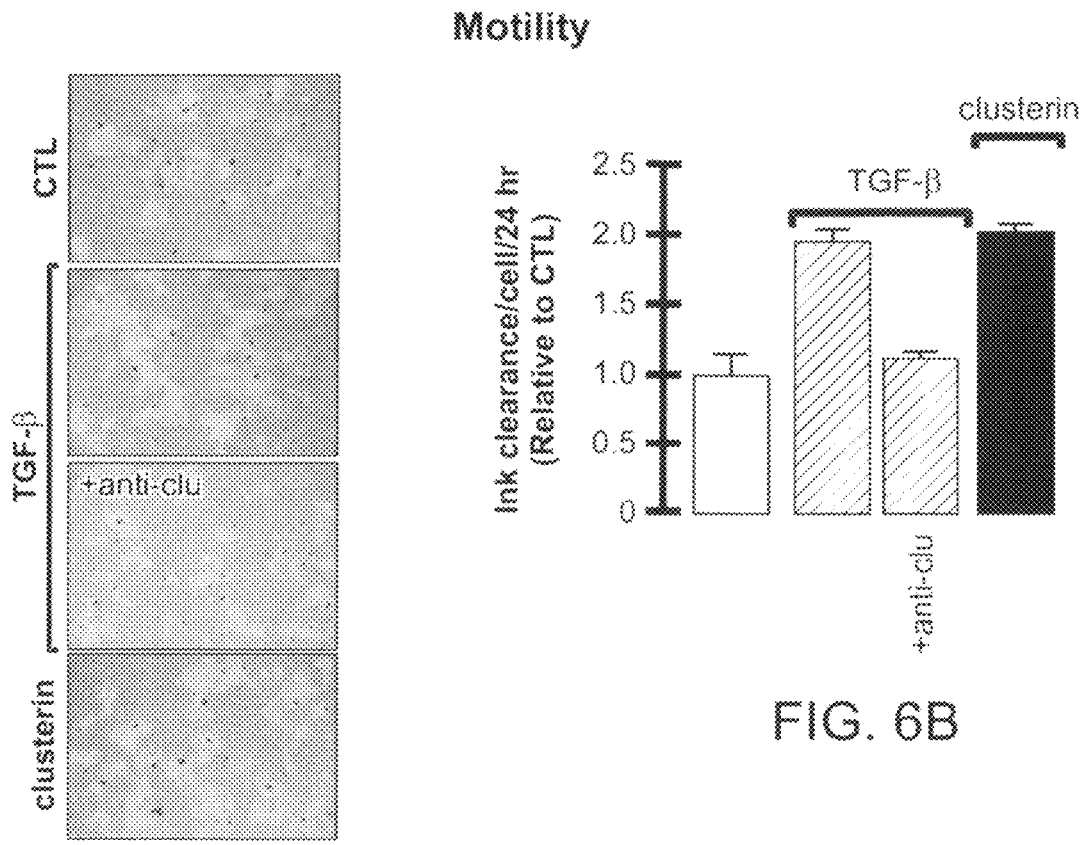
FIG. 6A
FIG. 6B
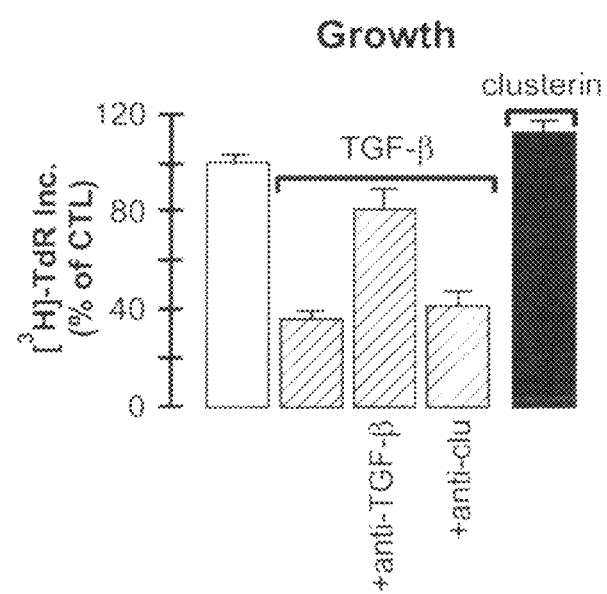
FIG. 6C

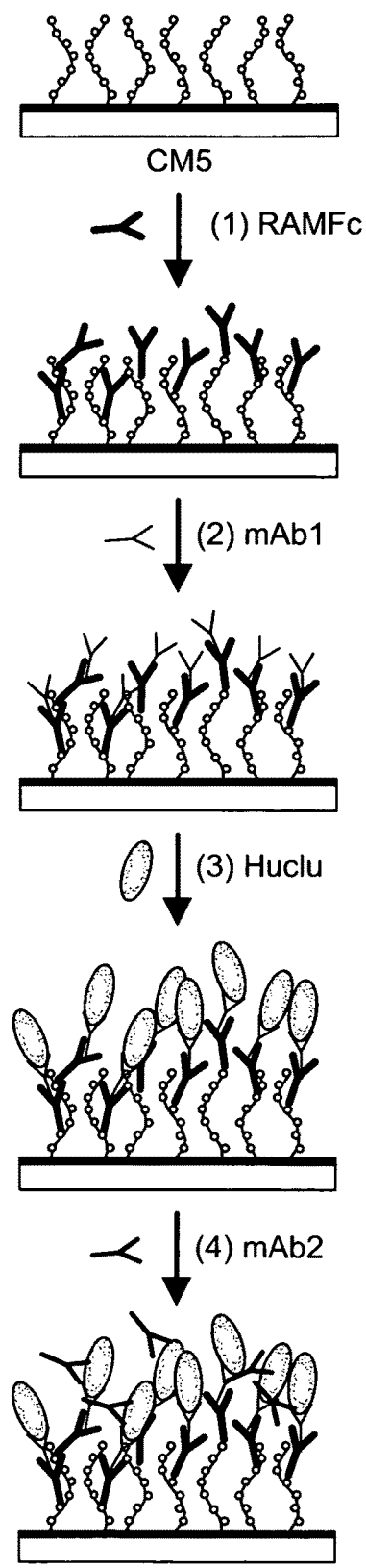
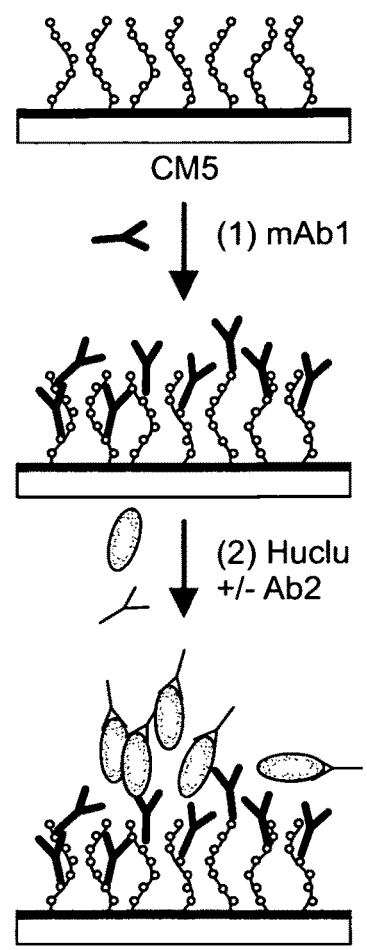
FIG. 10B
FIG. 10A

|  | Antibody 1 (immobilized directly or indirectly) | | | |
|---|---|---|---|---|
|  | 16B5 | 16C11 | 20 E 11 | 21B12 |
| Antibody 2 -interacting with clusterin (in solution or captured on Ab1) |  |  |  |  |
|  |  |  |  |  |
| Neutralizing mAb |  |  |  |  |
| 16B5 | +    + | +    + | +    -* | +    + |
| 16C11 | +    + | +    + | +    -* | +    + |
| 20 E 11 | +    -* | ±    + | +    + | +    + |
| 21B12 | +    + | +    + | +    + | +    + |
| B5 | +    + | ±    + | +    + | +    + |
| 11E2 |    + |    + | -* |    + |
| Neutralizing pAb |  |  |  |  |
| C18 | + | + | + | + |
| pAb#10 | ± | ± | ± | ± |
|  |  |  |  |  |

| CLONE | Sequence | SEQ ID NO. |
|---|---|---|
| 11E2 VL Gr1 | ENVLTQSPAIMSASPGEKVTMTCSASSSVSYMHWYQQKSSTSPKLWIYDTSKLASGVPGRFSGSGSGNSYSLTISSMEAEDVATYYCFQGSGYPFTFGSGTKLEIK | SEQ ID NO.:8 |
| 11E2 VL Gr2 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLRTFGGGTKLEIK | SEQ ID NO.:9 |
| 20E11 VL | DIVLTLSPASLAVSLGQRATISCRASQSVNSSNYSYMHWYQQKPGQPPKLLIKYASNLESGVPARFSGSGSGTHFTLNIHPVEEEDTATYYCQHSWEIPWTFGGGTKLEIK | SEQ ID NO.:10 |
| 21B12 VL | DIVMSQSPSSLAVSVGEKVTMSCKSSQSLLYSSNQKNYLAWYQQRPGQSPKLLIYWASTRESGVPDRFTGSGSGTDFTLTISSVKAEDLAVYYCQQYYIYPRTFGGGTKLEIK | SEQ ID NO.:11 |
| 16B5 VL | DIVMSQSPSSLAVSAGEKVTMSCKSSQSLLNSRTRKNYLAWYQQKPGQSPKLLIYWASTRESGVPDRFTGSGSGTDFTLTISSVQAEDLAVYYCKQSYNLWTFGGGTKLEFK | SEQ ID NO.:12 |
| 7C12 VL | DVLMTQTPLSLPVSPGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | SEQ ID NO.:13 |
| 6E12 VL | DVVLTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHIPRTFGGGTKLEIK | SEQ ID NO.:14 |
| 7B7 VL | DIVMTQSPSSLAMSVGQRVTMSCKSSQSLLNSNNQKNYLAWYQQKPGQSPKLLVYFASTRESGVPDRFIGSGSGTDFTLTISSVQAEDLADYFCQQHYNTPLTFGAGTKLELK | SEQ ID NO.:15 |
| 7D6 VL | DVVMTQTPLSLPVSLGDQASISCRSSQSLVHSNGDTYLHWYLQKPGQSPKLLIYKVSNRFSGVPDRFSGSGSGTDFTLKISRVEAEDLGVYFCSQSTHVPRTFGGGTKLEIK | SEQ ID NO.:16 |

FIG. 13 Cont.

| CLONE | Sequence | SEQ ID NO. |
|---|---|---|
| 8F6 VL | DVLLTQTPLSLPVSLGDQASISCRSSQSLVHSNGNTYLHWYLQKPGQSPKLLIYKVSNRFSGVPDRFSGSGSGTDFTLNISRVEAEDLGVYFCSQSTHVPRTFGGGTKLEIK | SEQ ID NO.:17 |
| 18F4 VL | DIVMTQSPATLSVTPGDRVSLSCRASQSISDYLHWYQQKSHESPRLLIKYASQSISGIPSRFSGSGSGSDFTLSINSVEPEDVGVYYCQNGHSFPYTFGGGTKLEIK | SEQ ID NO.:18 |
| 20G3 VL | EIVLTQSPTTMTASPGEKITITCSASSSISSNFLHWYQQKPGFSPKLLIYRTSNLPSGVPPRFSGSGSGTSYSLTIGTMEAEDVATYYCQQGSSLPRTFGAGTKLALK | SEQ ID NO.:19 |
|  |  |  |
| 16C11 VL |  |  |

FIG. 13 Cont.

| CLONE | Sequence | SEQ ID NO. |
|---|---|---|
| 11E2 VH | EVQLQQSGPELEKPGASVKISCKASGYSFTGYNMNW VKQNNGKSLEWIGNIDPYYGTPNYNQKFKGKATLTVD KSSSTAYMQLKSLTSEDSAVYYCALNSLLRLNAMDYW GQGTSVTVSS | SEQ ID NO.:20 |
| 20E11 VH | QIQLVQSGPELKKPGETVKISCKASGYTFTDYSMHWV KQAPGKGLKWMGWINTETGEPTYADDFKGRFAFSLE TSASTAYLQINNLKNEDTATYFCARTGSSGYFDCWGQ GTTLTVSS | SEQ ID NO.:21 |
| 21B12 VH | QIQLVQSGPELKKPGETVKISCKASGYTFTNYGMHWV KQAPGKGLKWMGWINTYTGEPTYADDFKGRFAFSLET SASTAYLQINNLKNEDTATYFCARDGFLYFFDYWGQG TTLTVSS | SEQ ID NO.:22 |
| 16B5 VH | EVQLQQSGAELVKPGASVRLSCTTSGFNIKDIYMHWV KQRPEQGLEWIGRIDPAYGNTKYDPKFQGKATITADT SSNTAYLQLSSLTSEDTAVYYCARRYDTAMDYWGQG TSVTVSS | SEQ ID NO.:23 |
| 16C11 VH | EVQLQQSGPELGKPGASVKISCKASGYSFTGYNMYW VKQSHRKSLEWIGYIDPYNGDTSYNQKSKGKATLTAD RSSSTAYMHLNSLTSEDSGIYYCARGAYGSSYAYWGQ GTLVAVSA | SEQ ID NO.:24 |
| 7C12 VH | EVQLVESGGGLVKPGGSLKLSCAASGFTFSSYAMSW VRQSPEKRLEWVAEISSGGTYTYYPDTVTGRFTISRDN AKNTLYLEMSSLRSEDTAMYYCTRIYYDYGSWDGFAY WGQGTLVTVSA | SEQ ID NO.:25 |
| 6E12 VH | QVQLQQSGPQLVRPGASVKISCKASDYSFTTYWMHW VKQRPGQGLEWIGMIDPSDSETRLNQKFKDKATLTVD KSSSTAYMQLSSPTSEDSAVYYCSRDGNYRYYTLDFW GQGTSVTVSS | SEQ ID NO.:26 |
| 7B7 VH | TCKLVESGGGLVKPGGSLKLSCAASGFTFSSYSMSWV RQTPEKRLEWVATISTIGSYTDYPDSVKGRFTISRDNA KNTLYLQMSSLKSEDTAMYCCTREDYRYAWFAYWGQ GTLVTVSA | SEQ ID NO.:27 |
| 8F6 VH | QVQLQQSGPQLVRPGASVKISCKASDYSFTTYWMHW VKQRPGQGLEWIGMIDPSDSETRLNQKFKDKATLTVD KSSSTAYMQLSSPTSEDSAVYYCSRDGNYRSYTMDY WGQGTSVTVSS | SEQ ID NO.:28 |

FIG. 13 Cont.

| CLONE | Sequence | SEQ ID NO. |
|---|---|---|
| 18F4 VH | EVQLVESGGGLVKPGGSLKFSCAASGFTFINYAMSWVRQSPEKRLEWIAEISSGGSDTYYPDTVTGRFTISRDNAKNTL*LEMSSLRSEDTAMYYCARDGNWDGGSLTTGAKAPLS | SEQ ID NO.:29 |
| 20G3 VH | QIQLVQSGPELKKPGETVKISCKASGYTLTDYSMHWVKQAPGKGLKWMGWINTETGEPTYVDDFKRRFAFSLETSASAAYLQINNLKNEDTATYFCTRDGSSTWFSYWGQGTLVTVSA | SEQ ID NO.:30 |

FIG. 13 Cont.

| CLONE | Frame 1 | CDR1 |
|---|---|---|
| 11E2 VL Gr1 | ENVLTQSPAIMSASPGEKVTMTCSAS (SEQ ID NO.: 53) | SSVSY (SEQ ID NO.:61) |
| 11E2 VL Gr2 | DIQMTQSPSSLSASLGGKVTITCKAS (SEQ ID NO.:54) | QDINKY (SEQ ID NO.:62) |
| 20E11 VL | DIVLTLSPASLAVSLGQRATISCRAS (SEQ ID NO.:55) | QSVNSSNYSY (SEQ ID NO.:63) |
| 21B12 VL |  | QSLLYSSNQKNY (SEQ ID NO.:64) |
| 16B5 VL | DIVMSQSPSSLAVSAGEKVTMSCKSS (SEQ ID NO.:56) | QSLLNSRTRKNY (SEQ ID NO.:65) |
| 7C12 VL | DVLMTQTPLSLPVSPGDQASISCRSS (SEQ ID NO.:57) | QSIVHSNGNTY (SEQ ID NO.:66) |
| 6E12 VL | DVVLTQTPLSLPVSLGDQASISCRSS (SEQ ID NO.:58) | QSLVHSNGNTY (SEQ ID NO.:67) |
| 7B7 VL | DIVMTQSPSSLAMSVGQRVTMSCKSS (SEQ ID NO.:59) | QSLLNSNNQKNY (SEQ ID NO.:68) |
| 7D6 VL | DVVMTQTPLSLPVSLGDQASISCRSS (SEQ ID NO.:60) | QSLVHSNGDTY (SEQ ID NO.:69) |

FIG. 13 Cont.

| CLONE | Frame 1 | CDR1 |
|---|---|---|
| 8F6 VL | DVLLTQTPLSLPVSLGDQASISCRSS (SEQ ID NO.:70) | QSLVHSNGNTY (SEQ ID NO.:73) |
| 18F4 VL | DIVMTQSPATLSVTPGDRVSLSCRAS (SEQ ID NO.:71) | QSISDY (SEQ ID NO.:74) |
| 20G3 VL | EIVLTQSPTTMTASPGEKITITCSAS (SEQ ID NO.:72) | SSISSNF (SEQ ID NO.:75) |
| | | |
| 16C11 VL | | |

FIG. 13 Cont.

| CLONE | Frame 1 | CDR1 |
|---|---|---|
| 11E2 VH | EVQLQQSGPELEKPGASVKISCKAS (SEQ ID NO.:76) | GYSFTGYN (SEQ ID NO.:85) |
| 20E11 VH | QIQLVQSGPELKKPGETVKISCKAS (SEQ ID NO.:77) | GYTFTDYS (SEQ ID NO.:86) |
| 21B12 VH | QIQLVQSGPELKKPGETVKISCKAS (SEQ ID NO.:78) | GYTFTNYG (SEQ ID NO.:87) |
| 16B5 VH | EVQLQQSGAELVKPGASVRLSCTTS (SEQ ID NO.:79) | GFNIKDIY (SEQ ID NO.:88) |
| 16C11 VH | EVQLQQSGPELGKPGASVKISCKAS (SEQ ID NO.:80) | GYSFTGYN (SEQ ID NO.:89) |
| 7C12 VH | EVQLVESGGGLVKPGGSLKLSCAAS (SEQ ID NO.:81) | GFTFSSYA (SEQ ID NO.:90) |
| 6E12 VH | QVQLQQSGPQLVRPGASVKISCKAS (SEQ ID NO.:82) | DYSFTTYW (SEQ ID NO.:91) |
| 7B7 VH | TCKLVESGGGLVKPGGSLKLSCAAS (SEQ ID NO.:83) | GFTFSSYS (SEQ ID NO.:92) |
| 8F6 VH | QVQLQQSGPQLVRPGASVKISCKAS (SEQ ID NO.:84) | DYSFTTYW (SEQ ID NO.:93) |

FIG. 13 Cont.

| CLONE | Frame 1 | CDR1 |
|---|---|---|
| 18F4 VH | EVQLVESGGGLVKPGGSLKFSCAAS (SEQ ID NO.:94) | GFTFINYA (SEQ ID NO.:96) |
| 20G3 VH | QIQLVQSGPELKKPGETVKISCKAS (SEQ ID NO.:95) | GYTLTDYS (SEQ ID NO.:97) |

FIG. 13 Cont.

| CLONE | Frame 2 | CDR2 |
|---|---|---|
| 11E2 VL Gr1 | MHWYQQKSSTSPKLWIY (SEQ ID NO.:98) | DTS |
| 11E2 VL Gr2 | IAWYQHKPGKGPRLLIH (SEQ ID NO.:99) | YTS |
| 20E11 VL | MHWYQQKPGQPPKLLIK (SEQ ID NO.:100) | YAS |
| 21B12 VL | LAWYQQRPGQSPKLLIY (SEQ ID NO.:101) | WAS |
| 16B5 VL | LAWYQQKPGQSPKLLIY (SEQ ID NO.:102) | WAS |
| 7C12 VL | LEWYLQKPGQSPKLLIY (SEQ ID NO.:103) | KVS |
| 6E12 VL | LHWYLQKPGQSPKLLIY (SEQ ID NO.:104) | KVS |
| 7B7 VL | LAWYQQKPGQSPKLLVY (SEQ ID NO.:105) | FAS |
| 7D6 VL | LHWYLQKPGQSPKLLIY (SEQ ID NO.:106) | KVS |

FIG. 13 Cont.

| CLONE | Frame 2 | CDR2 |
|---|---|---|
| 8F6 VL | LHWYLQKPGQSPKLLIY (SEQ ID NO.:107) | KVS |
| 18F4 VL | LHWYQQKSHESPRLLIK (SEQ ID NO.:108) | YAS |
| 20G3 VL | LHWYQQKPGFSPKLLIY (SEQ ID NO.:109) | RTS |
| 16C11 VL | | |

FIG. 13 Cont.

| CLONE | Frame 2 | CDR2 |
|---|---|---|
| 11E2 VH | MNWVKQNNGKSLEWIGN (SEQ ID NO.:110) | IDPYYGTP (SEQ ID NO.:119) |
| 20E11 VH | MHWVKQAPGKGLKWMGW (SEQ ID NO.:111) | INTETGEP (SEQ ID NO.:120) |
| 21B12 VH | MHWVKQAPGKGLKWMGW (SEQ ID NO.:112) | INTYTGEP (SEQ ID NO.:121) |
| 16B5 VH | MHWVKQRPEQGLEWIGR (SEQ ID NO.:113) | IDPAYGNT (SEQ ID NO.:122) |
| 16C11 VH | MYWVKQSHRKSLEWIGY (SEQ ID NO.:114) | IDPYNGDT (SEQ ID NO.:123) |
| 7C12 VH | MSWVRQSPEKRLEWVAE (SEQ ID NO.:115) | ISSGGTYT (SEQ ID NO.:124) |
| 6E12 VH | MHWVKQRPGQGLEWIGM (SEQ ID NO.:116) | IDPSDSET (SEQ ID NO.:125) |
| 7B7 VH | MSWVRQTPEKRLEWVAT (SEQ ID NO.:117) | ISTIGSYT (SEQ ID NO.:126) |
| 8F6 VH | MHWVKQRPGQGLEWIGM (SEQ ID NO.:118) | IDPSDSET (SEQ ID NO.:127) |

FIG. 13 Cont.

| CLONE | Frame 2 | CDR2 |
|---|---|---|
| 18F4 VH | MSWVRQSPEKRLEWIAE<br>(SEQ ID NO.:128) | ISSGGSDT<br>(SEQ ID NO.:130) |
| 20G3 VH | MHWVKQAPGKGLKWMGW<br>(SEQ ID NO.:129) | INTETGEP<br>(SEQ ID NO.:131) |

FIG. 13 Cont.

| CLONE | Frame 3 | CDR3 (D Region) |
|---|---|---|
| 11E2 VL Gr1 | KLASGVPGRFSGSGSGNSYSLTISSMEAEDVATYYC (SEQ ID NO.:132) | FQGSGYPFT (SEQ ID NO.:141) |
| 11E2 VL Gr2 | TLQPGIPSRFSGSGSGRDYSFSISNLEPEDIATYYC (SEQ ID NO.:133) | LQYDNLLRT (SEQ ID NO.:142) |
| 20E11 VL | NLESGVPARFSGSGSGTHFTLNIHPVEEEDTATYYC (SEQ ID NO.:134) | QHSWEIPWT (SEQ ID NO.:143) |
| 21B12 VL | TRESGVPDRFTGSGSGTDFTLTISSVKAEDLAVYYC (SEQ ID NO.:135) | QQYYIYPRT (SEQ ID NO.:144) |
| 16B5 VL | TRESGVPDRFTGSGSGTDFTLTISSVQAEDLAVYYC (SEQ ID NO.:136) | KQSYNLWT (SEQ ID NO.:145) |
| 7C12 VL | NRFSGVPDRFSGSGSGTDFTLKISRVEAEDLGVYYC (SEQ ID NO.:137) | FQGSHVPYT (SEQ ID NO.:146) |
| 6E12 VL | NRFSGVPDRFSGSGSGTDFTLKISRVEAEDLGVYFC (SEQ ID NO.:138) | SQSTHIPRT (SEQ ID NO.:147) |
| 7B7 VL | TRESGVPDRFIGSGSGTDFTLTISSVQAEDLADYFC (SEQ ID NO.:139) | QQHYNTPLT (SEQ ID NO.:148) |
| 7D6 VL | NRFSGVPDRFSGSGSGTDFTLKISRVEAEDLGVYFC (SEQ ID NO.:140) | SQSTHVPRT (SEQ ID NO.:149) |

FIG. 13 Cont.

| CLONE | Frame 3 | CDR3 (D Region) |
|---|---|---|
| 8F6 VL | NRFSGVPDRFSGSGSGTDFTLNISRVEAEDLGVYFC<br>(SEQ ID NO.:150) | SQSTHVPRT<br>(SEQ ID NO.:153) |
| 18F4 VL | QSISGIPSRFSGSGSGSDFTLSINSVEPEDVGVYYC<br>(SEQ ID NO.:151) | QNGHSFPYT<br>(SEQ ID NO.:154) |
| 20G3 VL | NLPSGVPPRFSGSGSGTSYSLTIGTMEAEDVATYYC<br>(SEQ ID NO.:152) | QQGSSLPRT<br>(SEQ ID NO.:155) |
|  |  |  |
| 16C11 VL |  |  |

FIG. 13 Cont.

| CLONE | Frame 3 | CDR3 (D Region) |
|---|---|---|
| 11E2 VH | NYNQKFKGKATLTVDKSSSTAYMQLKSLTSEDSAVYY (SEQ ID NO.:156) | ALNSLLRLNAMDY (SEQ ID NO.:165) |
| 20E11 VH | TYADDFKGRFAFSLETSASTAYLQINNLKNEDTATYFC (SEQ ID NO.:157) | ARTGSSGYFDC (SEQ ID NO.:166) |
| 21B12 VH | TYADDFKGRFAFSLETSASTAYLQINNLKNEDTATYFC (SEQ ID NO.:158) | ARDGFLYFFDY (SEQ ID NO.:167) |
| 16B5 VH | KYDPKFQGKATITADTSSNTAYLQLSSLTSEDTAVYYC (SEQ ID NO.:159) | ARRYDTAMDY (SEQ ID NO.:168) |
| 16C11 VH | SYNQKSKGKATLTADRSSSTAYMHLNSLTSEDSGIYY (SEQ ID NO.:160) | ARGAYGSSYAY (SEQ ID NO.:169) |
| 7C12 VH | YYPDTVTGRFTISRDNAKNTLYLEMSSLRSEDTAMYYC (SEQ ID NO.:161) | TRIYYDYGSWDGFAY (SEQ ID NO.:170) |
| 6E12 VH | RLNQKFKDKATLTVDKSSSTAYMQLSSPTSEDSAVYY (SEQ ID NO.:162) | SRDGNYRYYTLDF (SEQ ID NO.:171) |
| 7B7 VH | DYPDSVKGRFTISRDNAKNTLYLQMSSLKSEDTAMYC (SEQ ID NO.:163) | TREDYRYAWFAY (SEQ ID NO.:172) |
| 8F6 VH | RLNQKFKDKATLTVDKSSSTAYMQLSSPTSEDSAVYY (SEQ ID NO.:164) | SRDGNYRSYTMDY (SEQ ID NO.:173) |

FIG. 13 Cont.

| CLONE | Frame 3 | CDR3 (D Region) |
|---|---|---|
| 18F4 VH | YYPDTVTGRFTISRDNAKNTL*LEMSSL RSEDTAMYYC (SEQ ID NO.:174) | ARDGNWDGGSLT (SEQ ID NO.:176) |
| 20G3 VH | TYVDDFKRRFAFSLETSASAAYLQINNL KNEDTATYFC (SEQ ID NO.:175) | TRDGSSTWFSY (SEQ ID NO.:177) |

FIG. 13 Cont.

| CLONE | Frame 4 (J Region) | |
|---|---|---|
| 11E2 VL Gr1 | GSGTKLEIK (SEQ ID NO.:178) | |
| 11E2 VL Gr2 | FGGGTKLEIK (SEQ ID NO.:179) | |
| 20E11 VL | FGGGTKLEIK (SEQ ID NO.:180) | |
| 21B12 VL | FGGGTKLEIK (SEQ ID NO.:181) | |
| 16B5 VL | FGGGTKLEFK (SEQ ID NO.:182) | |
| 7C12 VL | FGGGTKLEIK (SEQ ID NO.:183) | |
| 6E12 VL | FGGGTKLEIK (SEQ ID NO.:184) | |
| 7B7 VL | FGAGTKLELK (SEQ ID NO.:185) | |
| 7D6 VL | FGGGTKLEIK (SEQ ID NO.:186) | |

FIG. 13 Cont.

| CLONE | Frame 4 (J Region) | |
|---|---|---|
| 8F6 VL | FGGGTKLEIK<br>(SEQ ID NO.:187) | |
| 18F4 VL | FGGGTKLEIK<br>(SEQ ID NO.:188) | |
| 20G3 VL | FGAGTKLALK<br>(SEQ ID NO.:189) | |
| 16C11 VL | | |

FIG. 13 Cont.

| CLONE | Frame 4 (J Region) | J Region (frameshift) |
|---|---|---|
| 11E2 VH | WGQGTSVTVSS (SEQ ID NO.:190) | |
| 20E11 VH | WGQGTTLTVSS (SEQ ID NO.:191) | GAKAPLSQSPQ (SEQ ID NO.:199) |
| 21B12 VH | WGQGTTLTVSS (SEQ ID NO.:192) | |
| 16B5 VH | WGQGTSVTVSS (SEQ ID NO.:193) | LWTTGVKEPQSPSPQ (SEQ ID NO.:200) |
| 16C11 VH | WGQGTLVAVSA (SEQ ID NO.:194) | LLGPRDSGRCLC (SEQ ID NO.:201) |
| 7C12 VH | WGQGTLVTVSA (SEQ ID NO.:195) | |
| 6E12 VH | WGQGTSVTVSS (SEQ ID NO.:196) | |
| 7B7 VH | WGQGTLVTVSA (SEQ ID NO.:197) | |
| 8F6 VH | WGQGTSVTVSS (SEQ ID NO.:198) | ILWTTGVKEPQSPSPQ (SEQ ID NO.:202) |

FIG. 13 Cont.

| CLONE | Frame 4 (J Region) | J Region (frameshift) |
|---|---|---|
| 18F4 VH | WGQGTTLTVSS<br>(SEQ ID NO.:51) | LTTGAKAPLSQSPQ<br>(SEQ ID NO.:203) |
| 20G3 VH | WGQGTLVTVSA<br>(SEQ ID NO.:52) | |

CDR1: G-Y-S/T-F-T-X-Y-X
CDR2: I-D/N-P/T-Y/E-X-G-X-P/T though the detected TGF-β induced EMT in JM01 cells is characterized by morphology changes, motility, and marker expression changes.

METHODS AND COMPOSITIONS FOR MODULATING TUMOR CELL ACTIVITY

RELATED APPLICATIONS

This is a national entry application claiming the benefit of PCT Application No. PCT/CA2006/001505, which claims priority to U.S. Provisional Application No. 60/716,086 Sept. 13, 2005.

FIELD OF THE INVENTION

The invention relates to antibodies, peptides and small molecules which bind clusterin, and their use in modulating tumor cell activity.

BACKGROUND OF THE INVENTION

Carcinomas, the most common human malignancy, arise from epithelial cells. Progression of epithelial cancers begins with the disruption of cell-cell contacts as well as the acquisition of a migratory (mesenchymal-like) phenotype. This phenomenon, which is called an epithelial-to-mesenchymal transition (EMT), is considered to be a crucial event in late stage tumor progression and metastasis.

The secreted protein TGF-β suppresses tumor growth initially largely due to its growth inhibitory action on tumor cells of epithelial origin, then at later stages promotes tumor cell progression and metastasis. One mechanism by which TGF-β can promote tumor progression is through the induction of an EMT.

Due to the dual role that TGF-β plays in carcinogenesis, direct inhibitors of TGF-β may be risky since, while they could benefit late stage tumors, they could also accelerate preneoplastic lesions. A better therapeutic may be one that inhibits the pro-oncogenic EMT-promoting action of TGF-β, while leaving the tumor suppressor growth-inhibitory action of TGF-β unaffected. To develop such an inhibitor it would be necessary to identify the point at which there is a bifurcation of the TGF-β signaling pathway such that the mediators in one branch of the pathway participate in the EMT response, but not the growth inhibitory response to TGF-β. Therapeutics that inhibit mediators that lie exclusively in the EMT-promoting branch of the TGF-β signaling pathway will reduce metastasis while having little or no effect on the acceleration of preneoplastic lesions.

No TGF-β signal pathway specific components have been generally identified that promote or mediate the EMT-promoting action of TGF-β, yet are not involved in the growth inhibitory action of TGF-β.

In contrast, an endogenous protein (the YY1 nuclear factor) has been identified that is able to interfere with (as opposed to promote) the protumorigenic EMT action of TGF-β, while leaving the tumor-suppressing action (growth inhibition) intact (Kurisaki et al., 2004).

Inhibitors that target TGF-β ligands, receptors and the Smad signaling proteins are known. Specifically, soluble receptor ectodomains, antibodies and other binding proteins are able to act as antagonists by interacting with TGF-β ligands and sequestering them away from cell surface receptors. Small molecules are available that inhibit the kinase activity of the Type I TGF-β receptor and endogenous inhibitors of the Smad signaling proteins are also known. Since all of these signaling pathway components are involved in both the pro- and anti-carcinogenic actions of TGF-β, these inhibitors that target them may benefit late stage tumors, however, they could also accelerate preneoplastic lesions.

BRIEF DESCRIPTION OF THE DRAWINGS

FIG. 3: Validation of the TGF-β modulation of selected gene expression and protein levels. (A) Semi-quantitative PCR confirmed the TGF-β-induced clusterin up-regulation and caveolin-1 down-regulation thereby validating the microarray analysis (microarray data shown below PCR results). (B) Western blot analysis of whole cell lysates of JM01 cells treated for 24 hrs with TGF-β demonstrated that these transcriptional changes result in increased clusterin (p-clu=pre-clusterin; s-clu=secreted mature clusterin) and decreased caveolin-1 (Cav-1) protein levels. (C) Immunofluorescent microscopy of JM01 cells treated for 24 hrs with TGF-β further confirmed these changes in clusterin and caveolin-1 protein levels through the visualization of these proteins in the intact cell. Nuclei are stained blue, caveolin-1 and clusterin are stained green and the F-actin fibers are stained red.

hatched bar: anti-clusterin; grey bar: purified clusterin). (D) The induction of the EMT by clusterin alone was further confirmed by using FACS analysis of the epithelial marker E-cadherin to monitor the EMT.

Figure 1A:
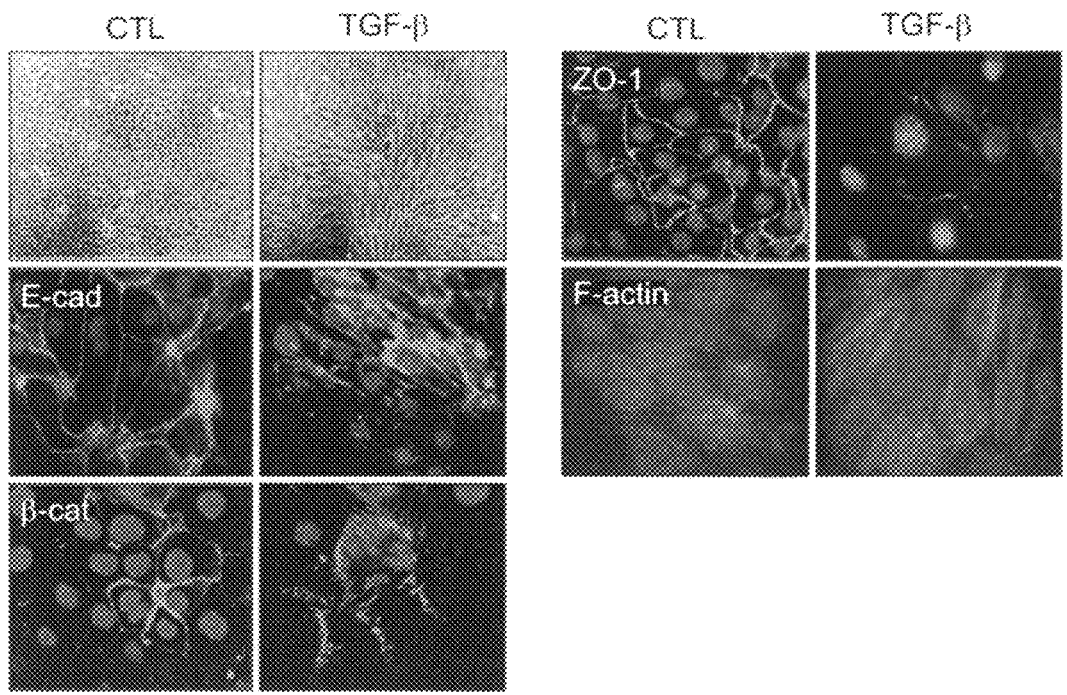
FIG. 1: TGF-β induces an epithelial to mesenchymal transition (EMT) in JM01 cells.
(A) This transition is characterized by an elongated morphology, the relocalization of the markers E-cadherin (E-cad), β-catenin (β-Cat) and F-actin and the down-regulation of the marker Zona Occludens-1 (ZO-1). (B) This morphology change is accompanied by an increase in cell motility as shown in a wound healing assay in which the cells' ability to migrate in to a 'scratch' area is monitored in the absence or presence of TGF-β. (C) A complementary black ink motility assay was also used to visualize and quantify the motility of individual JM01 cells in the absence or presence of TGF-β. The black ink which is coated on the plastic sticks to the migrating cells, thereby generating the white tracks. Both assays show that the presence of TGF-β increases the mobility of the JM01 cells.
Figure 1B:
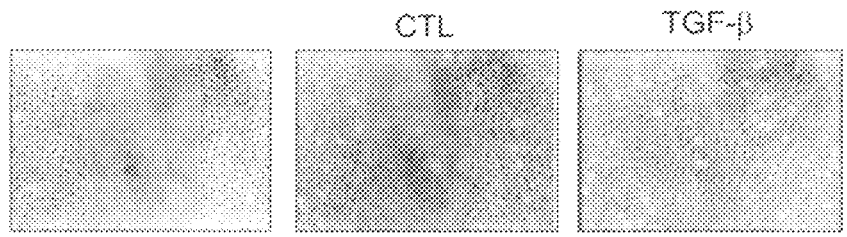
Figure 1C:
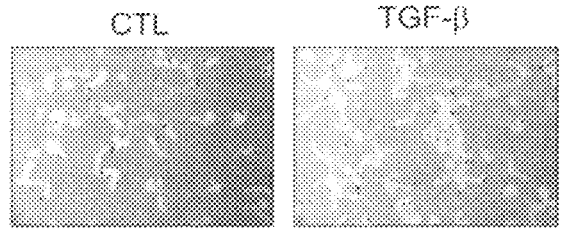
Figure 2A:
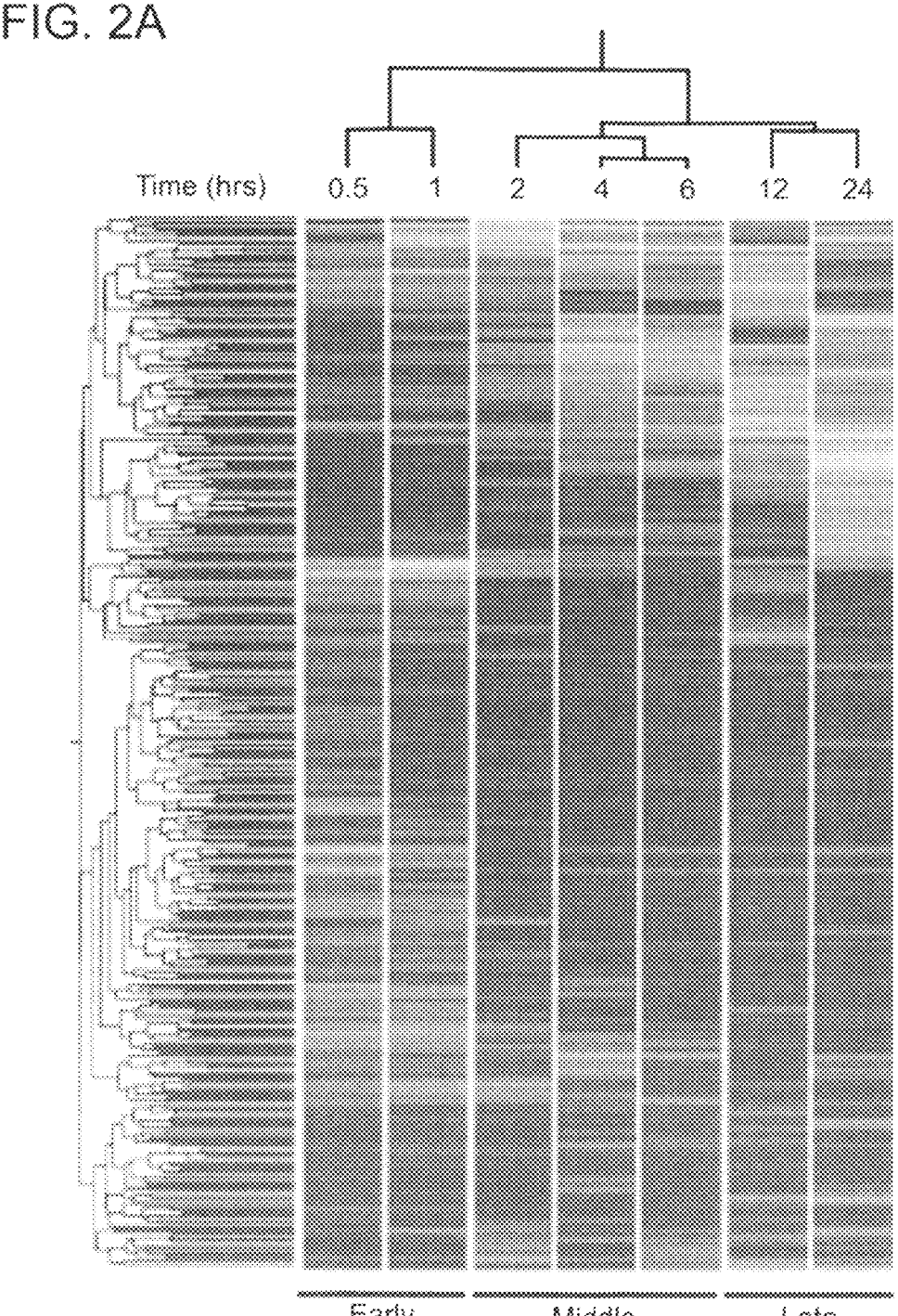
FIG. 2: Analysis of TGF-β-induced gene expression changes using microarray technology. (A) Extensive analysis of microarray data obtained from 7 time-points (0.5, 1, 2, 4, 6, 12, and 24 hrs) during the TGF-β induction of the JM01 cell EMT allowed for the identification of 328 genes that are modulated during the early (0.5, 1 hr), middle (2, 4, 6 hr) or late (12, 24 hr) stages of the transition. (B) Only 5 of these genes are affected over the entire time-course. (C) By comparing our gene list with data on the basal gene expression profiles of the NCI-60 cell line panel (some of these cell lines exhibit a mesenchymal phenotype), and with expression profiling data from clinical samples, we identified 15 genes from our list that are associated with a mesenchymal tumor cell phenotype and with clinical tumor progression.
Figures 2B, 2C:
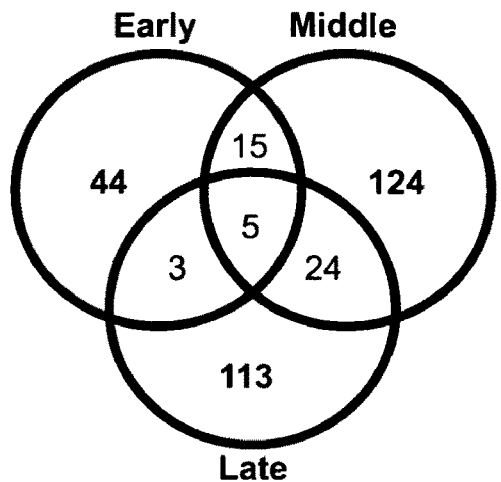
Figure 4A:
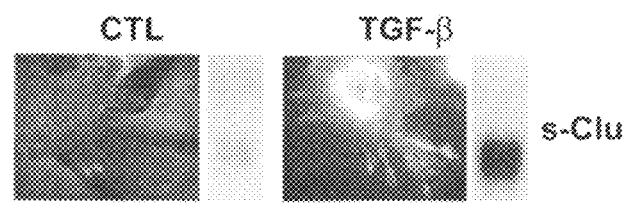
FIG. 4: Identification of secreted clusterin as a mediator of the TGF-β induced EMT. (A) Immunofluorescent microscopy indicated that clusterin is localized to the secretory pathway in JM01 cells and Western blot analysis of conditioned media (CM) indicated that clusterin is secreted (s-clu). (B, C) JM01 cells were treated for 24 hr with TGF-β, or CM taken from TGF-β treated JM01 cells, in the absence or presence of a antibody raised against the C-terminus of the clusterin β chain (anti-clu). Using immunofluorescent microscopy of ZO-1 as a marker of the EMT it was shown that the clusterin antibody blocks the induction of the EMT by both TGF-β and the CM indicating that secreted clusterin is a necessary mediator in the TGF-β EMT pathway. Purified clusterin alone was also shown to promote the EMT indicating that clusterin is not only necessary, but sufficient for the EMT induction (white bar: CTL, black bar: +anti-TGF-β.
Figure 4B:
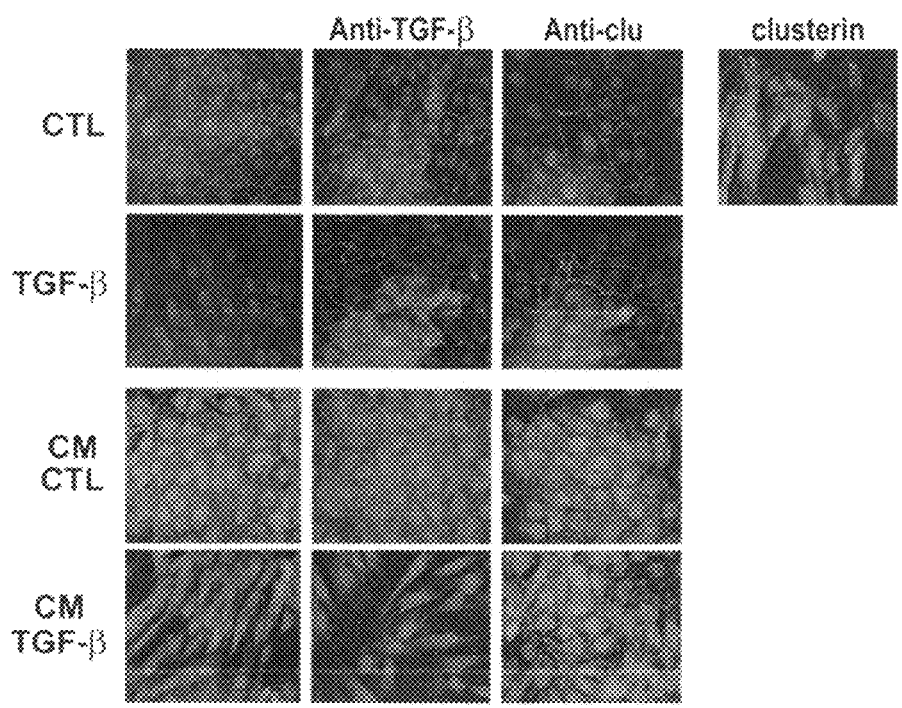
Figure 4C:
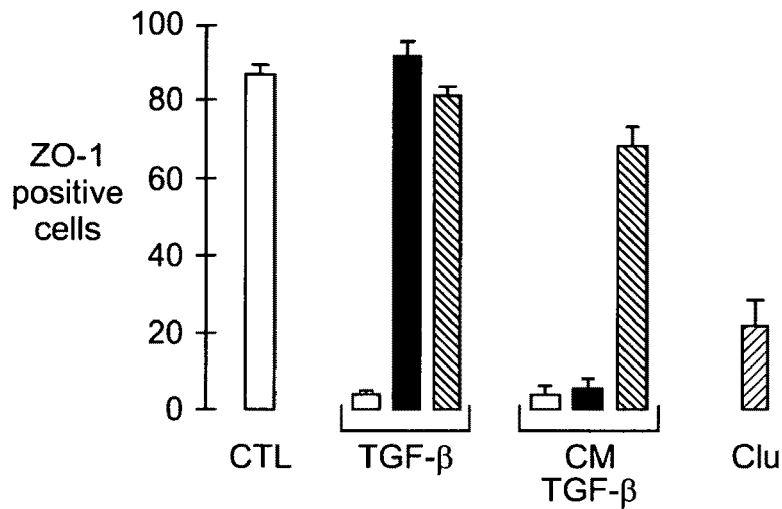
Figure 4D:
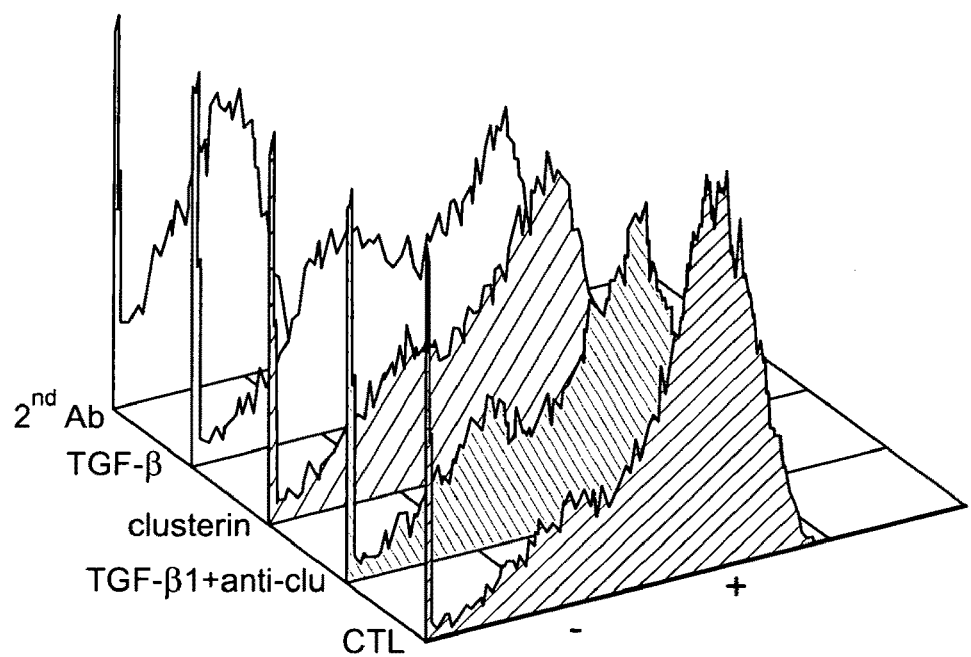
Figure 5:
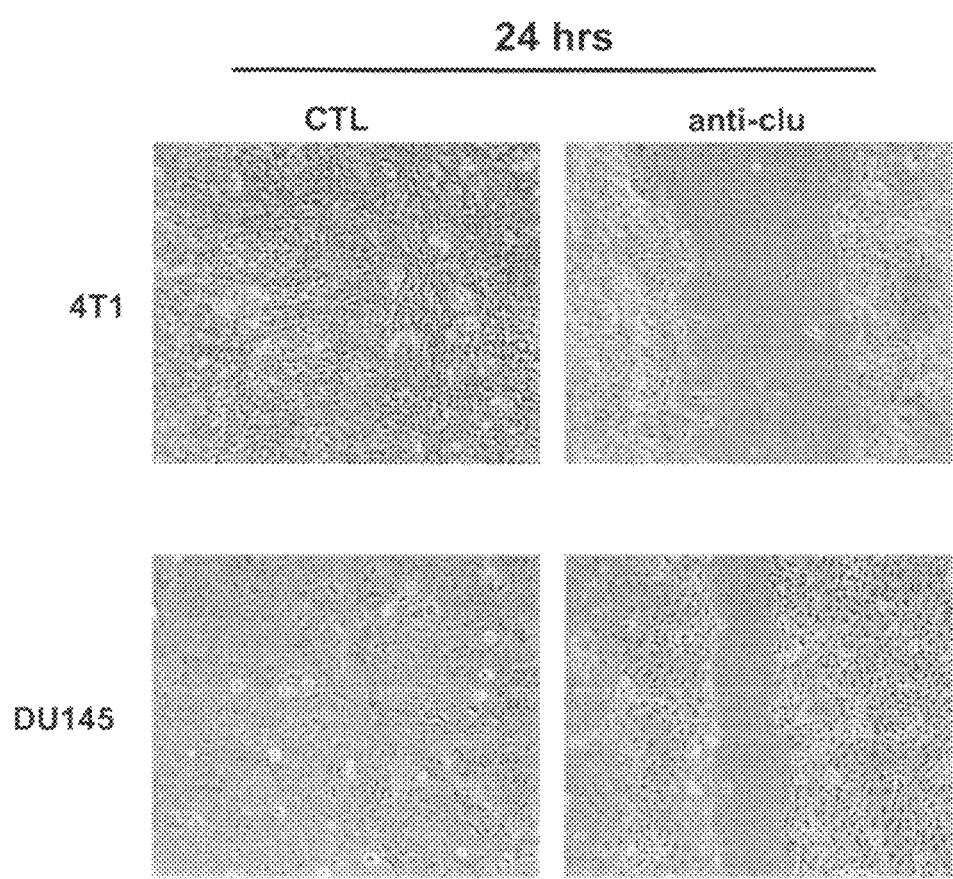

FIG. 5: Clusterin acts as an EMT mediator in cell lines other than the JM01 cells. 4T1 tumor cells (breast) and DU 145 tumor cells (prostate) were observed to secrete clusterin and exhibit a motile phenotype in the absence of TGF-β stimulation. Using the wound healing assay to monitor the motility of the 4T1 and DU145 cells, it was observed that a clusterin antibody (anti-clu) inhibits the motility of these cells indicating that clusterin is important for the maintenance of the TGF-β independent mesenchymal phenotype in these cells.

FIG. 6: Clusterin is a pivotal mediator in the pathway leading to TGF-β induction of EMT but not in the pathway leading to TGF-β growth inhibition. (A) Using the black ink motility assay to monitor the EMT of the JM01 cells, it was confirmed that a clusterin antibody blocks the TGF-β induced EMT and that clusterin alone promotes the EMT. (B) This result was further confirmed by quantifying the motility change as area cleared in the ink per cell. (C) In contrast, as monitored by the incorporation of tritiated thymidine, it was shown that the clusterin antibody does not block TGF-β induced growth inhibition and that clusterin alone does not promote growth inhibition, indicating that clusterin is not a mediator in TGF-β growth inhibitory pathways.

Figure 7:
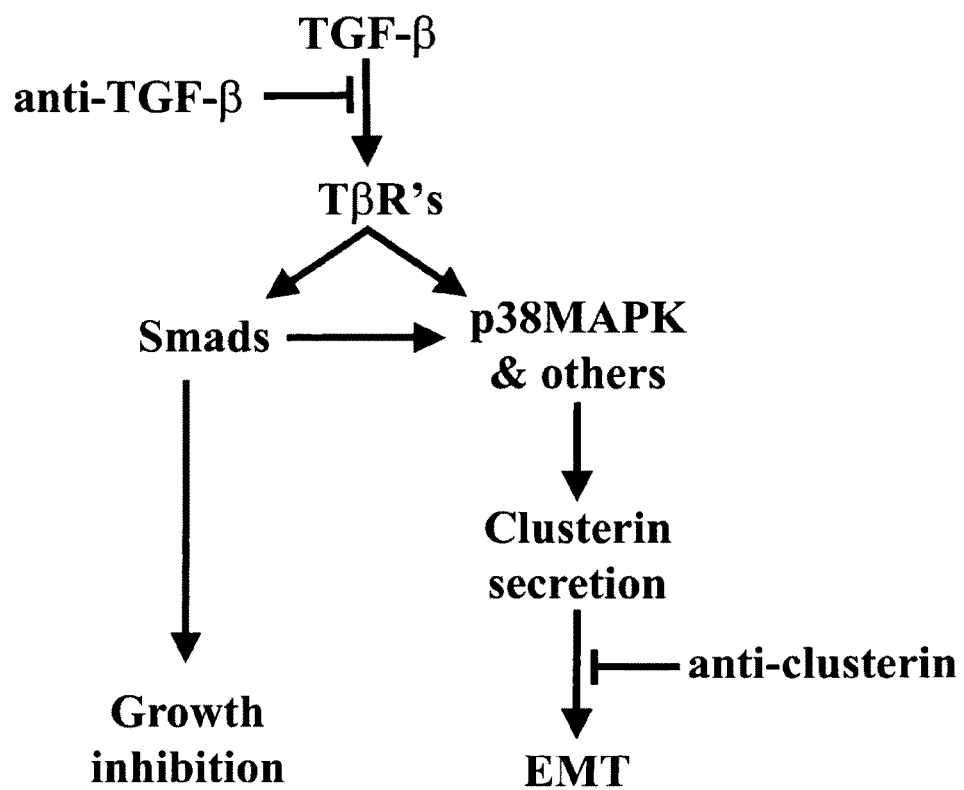

FIG. 7: Clusterin is an essential mediator in a TGF-β tumor promoting pathway but not in its tumor suppressing pathway. TGF-β induces secretion of clusterin and antibodies raised against the C-terminus of the clusterin β chain block the TGF-β1 induced EMT, but not the growth inhibitory response of the cells to TGF-β. These results indicate that clusterin is a necessary mediator in the TGF-β EMT pathway but do not address whether other TGF-β-induced mediators act in concert with clusterin to induce the EMT; that is, do not address the question of whether clusterin alone mediates an EMT. The fact that purified clusterin in the absence of TGF-β also promotes an EMT indicates that clusterin is sufficient to induce this transition.

Figure 8:
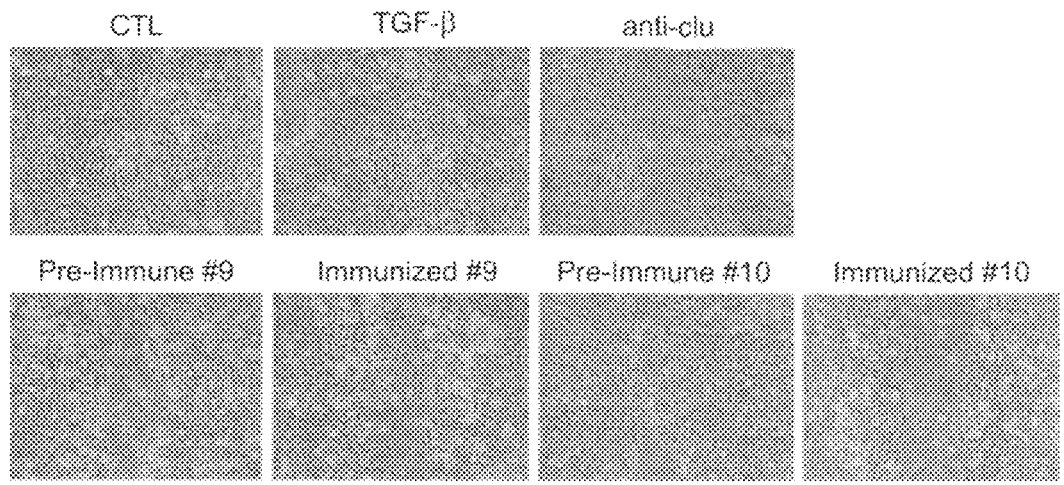
Figure 8:
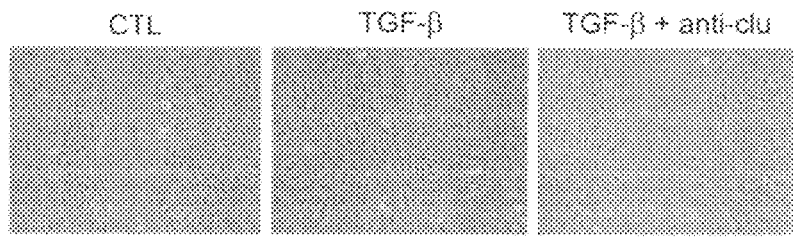
Figure 8:
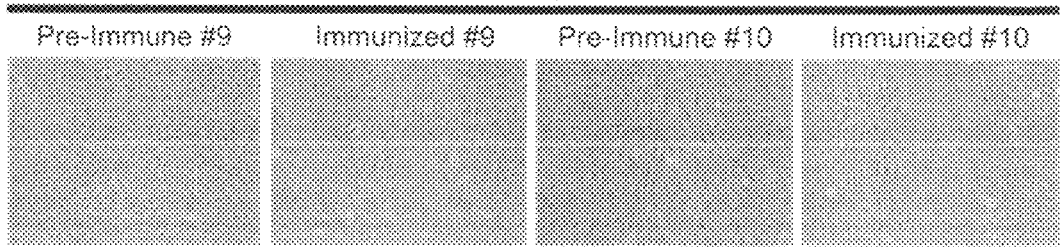

FIG. 8: Analysis of the neutralizing activity of anti-clusterin polyclonal antibodies produced at BRI. Sera collected from two rabbits (#9 and #10) immunized with a clusterin peptide (a.a. 421-437) were confirmed to contain antibodies that interact with the peptide using surface plasmon resonance (data not shown), and were tested for their ability to inhibit cell motility in a wound healing assay (1/25 dilution of rabbit serum). The mouse mammary epithelial cell line, 4T1 (top), secretes clusterin and is motile in the absence of TGF-β, whereas the JM01 cell line (bottom) requires stimulation with TGF-β to induce clusterin production and cell motility. The sera of both rabbit #9 and #10 inhibit motility, with #10 serum being more potent. As expected, the pre-immune sera of both rabbits does not affect motility. A commercially available clusterin antibody is shown as a positive control (anti-clu, Santa Cruz).

FIG. 9: Analysis of the activity of the anti-clusterin monoclonal antibodies produced at BRI. (A) Immunoprecipitations of recombinant human clusterin (500 ng) using either 50 or 100 ng of each of 12 BRI-produced monoclonal antibodies (commercial polyclonal (C18) and monoclonal (B5) antibodies were used as positive controls). Samples were analyzed on a 12% reducing SDS-PAGE. All antibodies were observed to interact with recombinant clusterin by immunoprecipitation. (B) Assessment of the ability of the 12 BRI-produced monoclonal antibodies to inhibit the TGF-βinduced motility of JM01 cells using the black ink motility assay (commercial polyclonal (C18) and monoclonal (B5) antibodies were used as positive controls). The bar graph shows the relative values of the motility of the TGF-6 treated BRI-JM01 cells in the presence of the various antibodies. Five BRI-produced monoclonal antibodies (21B12, 20E11, 16C11, 16B5 and 11E2) inhibit the TGF-β induced motility of the BRI-JM01 cells. Values are expressed as the clearance/cell/24 hr relative to that of the TGF-β treated (control) cells. The * illustrates the cut-off value that was used when assessing neutralizing ability. When using this cut-off value in the black ink motility assay, there was a good agreement with the evaluation of the neutralizing ability of the monoclonal antibodies when using the wound healing motility assay (data not shown).

FIG. 10: Two SPR-biosensor (Biacore) approaches to analysing the relationship between the epitopes of antibodies. (A) In the first approach, a rabbit anti-mouse Fc antibody (RAMFc) is covalently immobilized on the sensor chip and one monoclonal (termed mAb 1) is captured on the surface. After binding clusterin to mAb1, the second monoclonal antibody (termed mAb2) is flowed over the surface. If the epitopes of the two antibodies are overlapping, then mAb2 will not be able to bind to mAb1-bound clusterin. If the two antibodies have unrelated epitopes, then mAb2will be able to bind to mAb1-bound clusterin. (B) In the second approach, one monoclonal (termed mAb1) is covalently immobilized on the sensor chip surface. Clusterin is then incubated with a second antibody (monoclonal or polyclonal, termed mAb2) in solution and the complex is then flowed over mAb1. If the epitopes of the two antibodies are overlapping, then mAb2-bound clusterin will not be able to bind to mAb1.

FIG. 11: Results of the analysis of the relationship of the epitopes of the 5 EMT neutralizing BRI-produced anti-clusterin monoclonals antibodies with each other, and with the peptide epitopes of the C18, pAb#10 and B5 antibodies. This table summarizes all the epitope mapping results obtained using the two SPR-biosensor (Biacore) approaches. A blue + indicates that Ab1 competed with Ab2 for binding to clusterin in the first Biacore approach (i.e. the ratio of RUs of Ab2 to RUs of bound clusterin was 0.1 or less). A red + or +/− indicates that Ab2 competed with Ab1 for binding to clusterin in the second Biacore approach (i.e. the binding of clusterin to Ab1 was inhibited between 30-100% for +, and between 10-30% for +/−, when preincubated with Ab2). It is evident that all of the five neutralizing monoclonal antibodies (21B12, 20E11, 16C11, 16B5 and 11E2) interact with the overlapping peptide epitopes of pAb#10, pAbC18 and mAb B5 since they all compete for each other, and for pAb#10, pAbC18 and mAb B5. *It should be noted that all of the negative results from the first approach (blue −) occurred when Ab 20E11 was used (either as Ab1 or Ab2) indicating that this Ab did not behave well in that experimental set up. Therefore, for Ab 20E11, conclusions are taken primarily from the second experimental approach.

Figure 12:
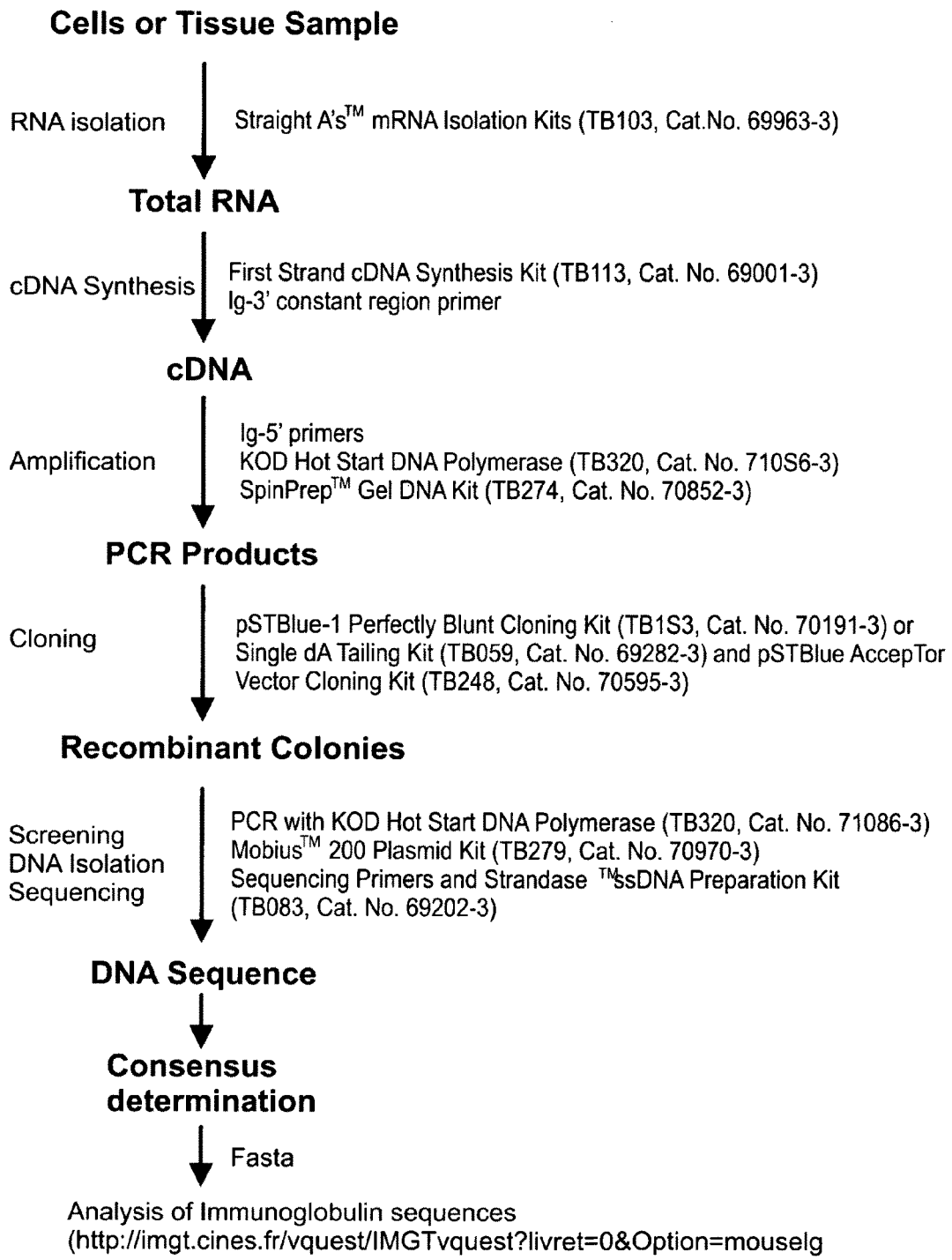

FIG. 12: Isolation of the Ig variable region cDNAs. Flow diagram indication the steps for the isolation, sequencing, sequence analysis of the monoclonal variable regions.

FIG. 13: Amino acid sequences of monoclonal antibodies

Figure 14:
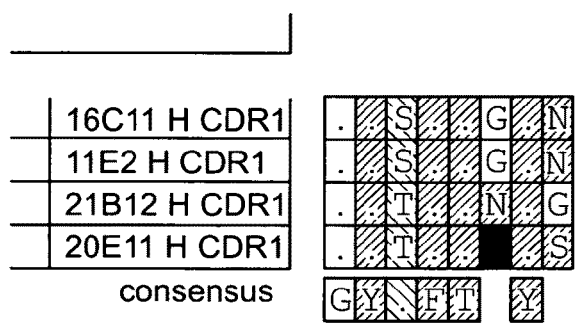
Figure 14:
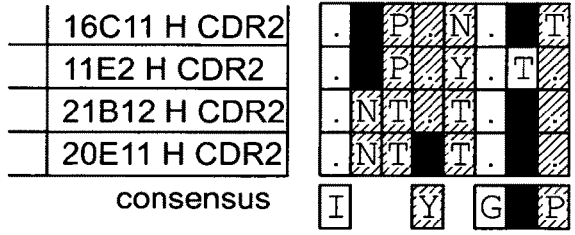

FIG. 14: CDR1 and CDR2 alignment of clusterin Ig VH

SUMMARY OF THE INVENTION

A first object of the invention is to identify a method for inhibiting EMT in tumour cells without inhibiting the tumour-suppressing activity of TGF-β.

A further object of the invention is to identify molecules or compositions which may inhibit TGF-β-induced EMT in tumour cells without inhibiting the tumour-suppressing activity of TGF-β.

A first aspect of the invention provides for an agent having a binding affinity for clusterin, wherein binding of the agent to clusterin inhibits epithelial-to-mesenchymal transition in carcinoma cells. In particular, the agent may bind to the β-subunit of clusterin, and more specifically, it may bind to the C-terminal portion of the clusterin β-subunit. The agent may, for example, be an antibody, including a monoclonal or polyclonal antibody.

A second aspect of the invention provides for a method for modulating the activity of carcinoma cells, comprising the steps of exposing the cells to an agent having a binding affinity for clusterin.

A further aspect of the invention provides for the use of an amino acid sequence in the generation of agents having a binding affinity for clusterin, wherein the sequence comprises SEQ ID NO.: 4 or a portion thereof. In particular, the sequence may comprise shorter portions of SEQ ID NO.: 4, including SEQ ID NO.: 1, SEQ ID NO.: 2, SEQ ID NO.: 3, and SEQ ID NO.: 5.

A further aspect of the invention provides for a vaccine comprising clusterin or a portion thereof which is involved in epithelial-to-mesenchymal transition in carcinoma cells, and a pharmaceutically suitable carrier. The portion of clusterin may comprise SEQ ID NO.: 4 or a portion thereof.

A further aspect of the invention provides for the use of an amino acid sequence in the preparation of a vaccine, wherein the sequence comprises SEQ ID NO.: 4 or a portion thereof. In particular, the sequence may comprise shorter portions of SEQ ID NO.: 4, including SEQ ID NO.: 1, SEQ ID NO.: 2, SEQ ID NO.: 3, and SEQ ID NO.: 5.

A further aspect of the invention provides for a nucleic acid sequence that encodes at least one of SEQ ID NO.: 1 through SEQ ID NO.: 30.

A further aspect of the invention provides for the use of an agent with a binding affinity for clusterin as a diagnostic tool, wherein binding of the agent to clusterin inhibits epithelial-to-mesenchymal transition in carcinoma cells.

DETAILED DESCRIPTION OF THE INVENTION

It is disclosed herein that clusterin is a therapeutic target whose inhibition blocks EMT without preventing TGF-β's anti-proliferative tumor suppressor action.

Clusterin was first identified as a protein possibly involved in EMT using transcriptome analysis, then was analyzed to identify potential binding sites within clusterin. Synthetic peptides were created accordingly, and antibody preparations directed against these peptides were produced or purchased. Additionally, twelve monoclonal antibodies were isolated using full-length recombinant clusterin as the antigen. Both the anti-peptide antibody preparations and the twelve monoclonal antibodies were confirmed to bind to recombinant clusterin. The anti-peptide polyclonal antibody preparations and five of the twelve monoclonal antibodies were shown to inhibit EMT. These five neutralizing monoclonal antibodies were shown to interact with the same peptide epitope as the anti-peptide antibodies.

Using semi-quantitative RT-PCR, Western blot and immunofluorescent microscopy analysis, it was confirmed that several of the EMT-associated transcriptional changes that were detected by microarray analysis were reflected in changes in message and protein abundance (clusterin and caveolin are shown in FIG. 3). Anti-peptide antibodies were used to demonstrate that clusterin is an essential EMT mediator that is not involved in TGF-β's growth inhibitory pathways (FIGS. 4-6). These results indicate that clusterin is an accessible therapeutic target whose inhibition blocks EMT without preventing TGF-β's anti-proliferative tumor suppressor action.

The epitope within clusterin that is important for the generation of EMT-inhibiting agents was elucidated using anti-peptide antibody preparations in neutralization assays. Two different commercial polyclonal antibody preparations raised against synthetic peptides corresponding to sections of the C-terminus of the clusterin β sub-unit were used. The first antibody (from RDI Research Diagnostics Inc.) was raised against the synthetic peptide corresponding to amino acids 421-437 of clusterin (VEVSRKNPKF METVAEK, SEQ ID NO 1) (termed RDI) and the second antibody (from Santa Cruz Biotechnology Inc.) was raised against the synthetic peptide corresponding to amino acids 432-443 of clusterin (ETVAEKALQ EYR, SEQ ID NO 2) (termed C-18). An anti-peptide monoclonal antibody against the same peptide (SEQ ID NO 2) was also purchased (termed B5). The overlap between these two epitopes is shown below. The ability of these antibody preparations to block EMT indicates the significance of the C-terminal portion of the clusterin β subunit in inducing EMT (FIG. 4-6, C-18 results shown; similar results obtained with RDI).

```
375 LTQGED QYYLRVTTVA SHTSDSDVPS GVTEVVVKLF DSDPITVTVP VEVSRKNPKF METVAEKALQ EYRKKHREE 449
                                                        Antibody 1

Antibody 2
```

Prediction of Putative Functional Subdomains in Clusterin Based on Structural Bioinformatics Generally, clusterin is thought to be a protein that is only partially structured, containing molten globule fragments. Additionally, it has been classified as an intrinsically disordered protein. Clusterin is postulated to contain several independent classes of binding sites capable of interacting with numerous other binding partners.

The clusterin sequence was examined using bioinformatics programs, namely:
  PredictProtein (Rost, 1996).
  GenTHREADER (Jones, 1999).
  COILS (Lupas, 1996).
  PONDR (Li et al., 1999)

The C-terminal fragment of the β-subunit was identified as a putative binding region. The fragment (a.a. 375-449, SEQ ID NO.: 4), which starts after the second coiled-coil region, is likely unfolded but has some propensity for β-sheet formation.

A synthetic peptide was produced corresponding to a.a. 421-437 of clusterin in order to generate polyclonal antibody preparations at BRI that are similar to the commercial antibody 1 preparation (RDI) (these new polyclonal preparations are termed pAb#9 and #10). Additionally, full-length human clusterin was expressed in 293 cells and purified in order to use as antigen to generate monoclonal antibodies against full-length human clusterin. Twelve monoclonal antibodies were raised against full-length clusterin and were demonstrated to interact with clusterin by ELISA. These twelve antibodies are named 6E12, 7B7, 21B12, 20G3, 20E11, 18F4, 16C11, 16B5, 11E2, 8F6, 7D6, 7C12.

The polyclonal antibody preparations raised against the a.a. 421-437 epitope (pAb#9 and #10) were confirmed to inhibit the EMT (FIG. 8).

Figure 9A:
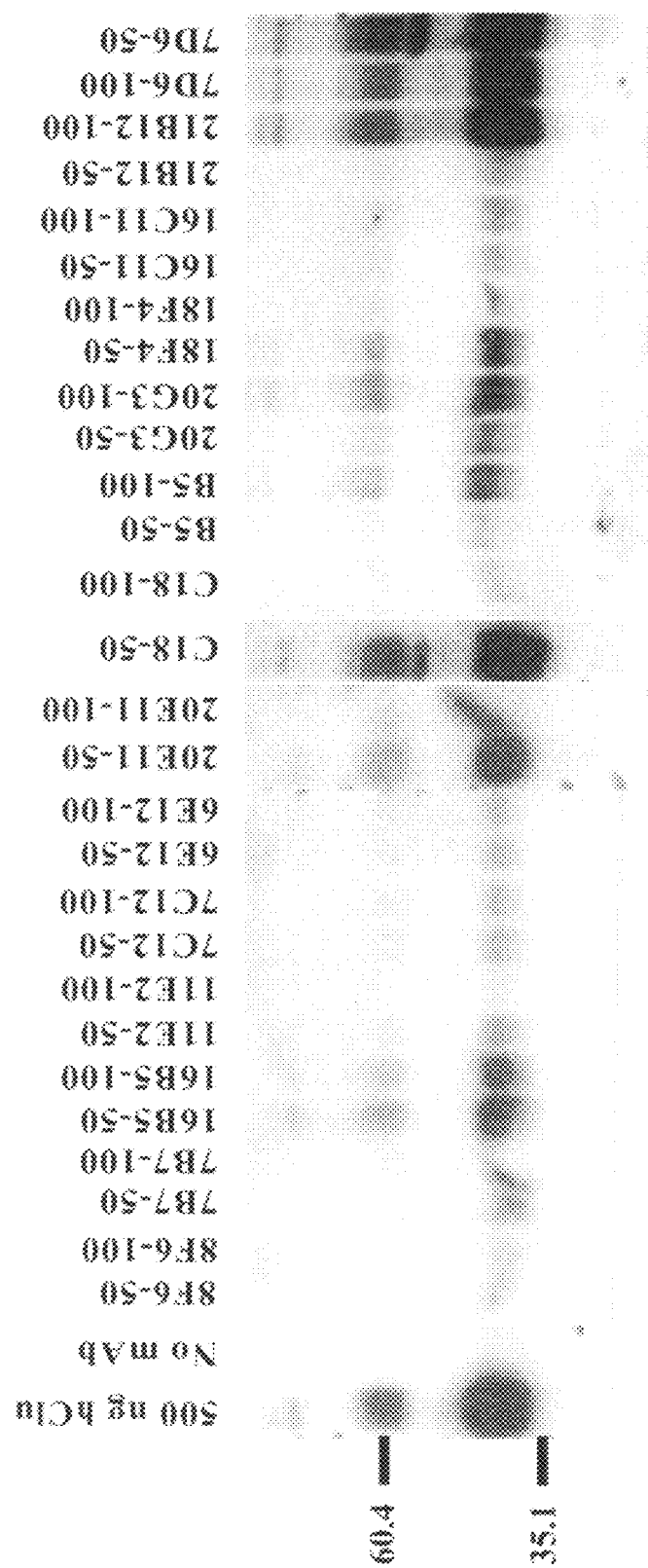
Figure 9B:
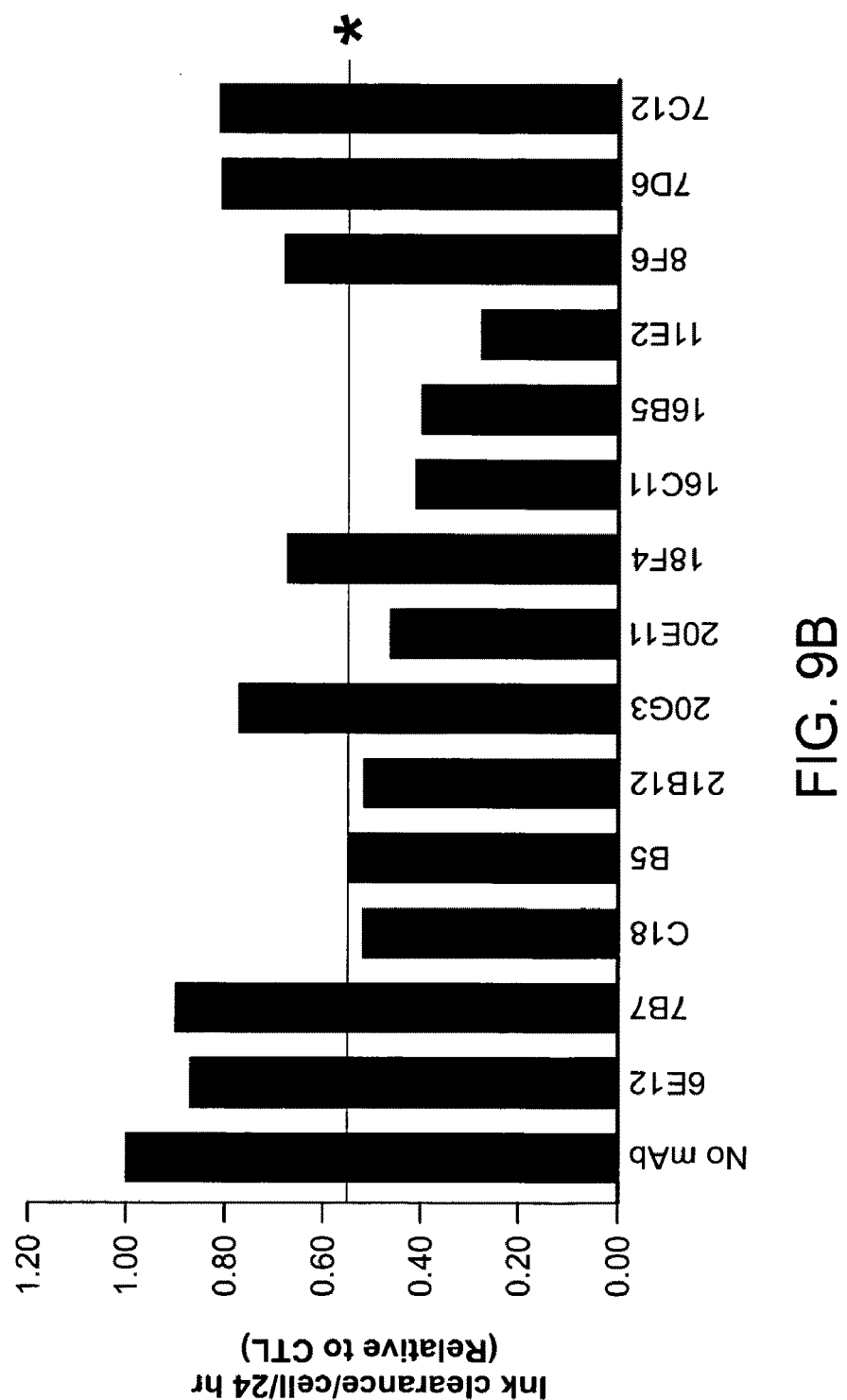

All twelve monoclonal antibody preparations raised against full-length human clusterin were confirmed to interact with recombinant human clusterin as evidenced by their ability to immunoprecipitate clusterin (FIG. 9A). Five of the twelve monoclonals were shown to be able to neutralize the EMT promoting action of clusterin in the black ink cell motility assay (FIG. 9B) and the wound healing cell motility assay (not shown). The five monoclonal antibodies that neutralize are 11E2, 21B12, 20E11, 16C11, 16B5.

Two Surface Plasmon Resonance (SPR)-based biosensor epitope mapping assays (FIG. 10) were used to determine whether the five neutralizing monoclonal antibodies generated using full-length clusterin were interacting with the same clusterin peptide epitope as the anti-peptide antibody preparations.

The two approaches that were used are described below:
1) The monoclonal antibodies were individually captured on a CM5 sensor chip surface on which a Rabbit-anti-Mouse Fc antibody was covalently immobilized (when captured, the mAb is termed mAb1 in this experimental approach). Clusterin was then allowed to bind to mAb1. Then all five monoclonal antibodies were sequentially injected over mAb1-bound clusterin (the injected mAb is termed mAb2 in this experimental approach) in order to determine if both mAb1 and mAb2 are able to interact with clusterin simultaneously (FIG. 11). It was found that all of the five neutralizing mAbs (except 20E11 in some cases) competed with each other for binding to clusterin (when used both as mAb1 or as mAb2). Additionally, they were found to compete with the C18, pAb#10 and B5 anti-peptide antibodies, suggesting that the five neutralizing mAbs interact with the overlapping peptide epitopes of pAb#10, pAbC18 and mAb B5. It should be noted that, although Ab 20E11 appeared to have a distinct epitope in some cases (when used either as mAb1 or mAb2), this conclusion was not supported by the results of the second experimental approach.
2) The monoclonal antibodies were individually covalently immobilized on a CM5 sensor chip surface using amine coupling (when immobilized, the mAb is termed mAb1 in this experimental approach). To demonstrate competition for binding to clusterin, an Ab (termed Ab2 in this approach) was then incubated with clusterin prior to injection of the complex over the mAb1 surface (FIG. 11).

It was confirmed that all of the five neutralizing mAbs competed with each other for binding to clusterin, and with the C18, pAb#10 and B5 anti-peptide antibodies. This confirms that the five neutralizing mAbs interact with the overlapping peptide epitopes of pAb#10, pAbC18 and mAb B5.

The hypervariable complementary determining regions (CDRs) of all twelve monoclonal Abs were sequenced. Mammalian light- and heavy-chain Igs contain conserved regions adjacent to the CDRs and the use of appropriately designed oligonucleotide primer sets enabled the CDRs to be specifically amplified using PCR (FIG. 12). These products were then sequenced directly (SEQ ID NO 8-30; see FIG. 13).

By aligning the CDR sequences of four out of the five neutralizing monoclonal antibodies (11E2, 21B12, 20E11, 16C11), we were able to determine a consensus sequence for VH CDR1 and CDR2 of these anti-clusterin antibodies (see FIG. 14). The following consensus sequences were determined: CDR-1: G-Y-S/T-F-T-X-Y-X (SEQ ID NO.: 6) and CDR-2: I-N/D-P/T-Y/E-X-G-X-P/T (SEQ ID NO.: 7).

The antibodies or peptides that interact with the epitope of clusterin defined here may be applied as therapeutics, i.e. they may act as a therapeutic in their own right due to their intrinsic ability to neutralize the EMT promoting activity of clusterin. Additionally, these antibodies and peptides may be used as a therapeutic due to their ability to target toxins, suicide genes or other agents with anti-tumor activity to the vicinity of tumor cells through their interaction with secreted clusterin.

Small molecules that interact with the epitope of clusterin defined here may also act as therapeutics by blocking the EMT promoting activity of clusterin. These antibodies, peptides and small molecules that exert their therapeutic activity by interacting with this clusterin epitope may exhibit less toxicity or side-effects as compared to other agents that remove all activities of clusterin, i.e. antisense or RNAi agents, since, while the EMT activity of clusterin is neutralized when this epitope is blocked, the other activities of clusterin may remain intact.

Other applications of the antibodies and peptides that interact with the epitope of clusterin defined here may be as 1) non-imaging diagnostics, i,e, they may detect clusterin as a biomarker in accessible body fluids or in tissue/tumor samples for diagnostic and prognostic applications in cancer, and 2) imaging diagnostics, i.e. they may be used to target contrast agents to tumors for imaging in vivo due to their interaction with secreted clusterin.

Antibodies comprising the heavy and light sequences identified herein, antibodies comprising the CDRs (complementarity determining regions) identified herein (FIG. 13), and antibodies comprising the consensus sequences (FIG. 14) are expected to be useful for the above-mentioned purposes.

Clusterin itself, or the portions thereof which contain the epitope recognized by the antibodies and peptides discussed above, may be used as a vaccine. Preferably, the clusterin should be combined with a pharmaceutically suitable carrier. Clusterin or epitope-containing portions of clusterin may also be used in the generation of vaccines. Similarly, amino acid sequences having at least 90% identity with SEQ ID NO. 4 or the clusterin epitope identified herein will also be useful, since they are likely to have similar functionality to the specific sequences identified herein.

Cell Culture, Antibodies and Reagents

BRI-JM01 cells were isolated and characterized as described (Lenferink et al., *Breast Cancer Res.*, 6, R514-30 (2004)). Cells were maintained at 37° C. in a humidified, 5% $CO_2$ atmosphere and cultured in DF/5% FBS (1:1 mixture of Ham's F12 and Dulbecco's modified Eagles Medium (DMEM) with 5% Fetal Bovine Serum (FBS) and antibiotics/antimicotics (both Wisent Inc.)).

Human recombinant TGF-β1 and pan-TGFβ neutralizing antibody 1D11 were reconstituted according to the manufacturer's instructions (R&D Systems). Purified human serum clusterin was kindly provided by Dr MR Wilson (Wilson and Easterbrook-Smith, 1992). Purified human recombinant clusterin was produced in HEK-293 cells (general expression system described in Durocher et al, 2002). Antibodies against the following proteins were purchased and used in the indicated v/v dilutions: E-cadherin (E-cad, anti-uvomorulin clone Decma-1; Sigma), Zona Occludens-1 (ZO-1; Chemicon), polyclonal antibodies raised against the C-terminus of the human clusterin β chain (cluβ; RDI and Santa Cruz), and Caveolin-1 (cav-1; Santa Cruz). Horseradish peroxidase (HRP) conjugated antibodies were obtained from Jackson ImmunoResearch Laboratories Inc. and Alexa-488 labeled antibodies and Texas-red labeled phalloidin were purchased from Molecular Probes. All experiments were carried out with 75-80% confluent monolayers of BRI-JM01 cells in DF/5%. Where indicated, cells were treated for 24 hr or 48 hr with TGF-β1 or purified clusterin at a final concentration of 100 pM or 200 nM, respectively.

RNA isolation and labeling

Monolayers of BRI-JM01 cells were grown in the absence or presence of TGF-β1 for 30 min, 1, 2, 4, 6, 12 or 24 hr. PolyA+mRNA was extracted (4×150 mm dishes per time point) using the FastTrack™2.0 kit (Invitrogen) according to the manufacturer's instructions. RNA was isolated and labeled according to Schade et al., 2004.

Hybridization and Data Analysis cDNA microarrays (15,264 sequence verified mouse ESTs were obtained from the University Health Network Microarray Center in Toronto. Slides were hybridized with Cy3 or Cy5 labeled cDNA as described (Enjalbert et al., 2003), scanned using a ScanArray 5000 (Perkin Elmer v2.11) at a 10-micron resolution and 16-bit TIFF files were quantified using QuantArray software (Perkin Elmer, v3.0). Microarray data normalization and analysis was performed as described (Enjalbert et al., 2003).

Northern Blot and Semi-Quantitative RT-PCR (SQ-RT-PCR) Analysis

For SQ-RT-PCR, 3-5 μg of total RNA was amplified in a 20 μl first-strand RT-PCR reaction using 50 U SuperScript II (Invitrogen) according to the manufacturer's guidelines with modifications. Samples were preincubated (2 min, 42° C.) before adding SuperScript II and the RNaseOUT treatment was omitted. Samples were incubated (90 min, 42° C.) and then cooled on ice. Two μl of first-strand reaction was added to the PCR mix (2.5 U Taq polymerase (New England Biolabs), 10 μM forward/reversed primers) in a final volume of 50 μl, which was heated (2 min, 94° C.) prior to PCR amplification. Primers for the generation of the probes used for northern blot and SQ-RT-PCR are listed in Table 1.

Western Blot Analysis

BRI-JM01 cells grown in 35 mm dishes were treated with TGF-β1 (24 hr). Cells were lysed in hot 2% SDS. Fifty μg of total protein or 30 μl of conditioned medium was resolved by SDS-PAGE (10%) under reducing conditions. Proteins were transferred to nitrocellulose and membranes incubated with primary antibodies (cluβ, cav-1; 1/500) in TBS-T (20 mM Tris-HCl (pH 7.6), 137 mM NaCl, 0.1% Tween 20 (v/v)) containing 5% non-fat milk (overnight, 4° C.). Membranes were washed with TBS-T, incubated with secondary HRP-conjugated antibody (1/20,000) in TBS-T+5% milk (1 hr), and washed with TBS-T. Immunoreactive bands were visualized using Enhanced Chemiluminescence (ECL; Perkin Elmer).

Immunofluorescence Microscopy

BRI-JM01 cells were seeded in glass chamber slides (Lab-Tek) and treated with purified clusterin or TGF-β1 preincubated (30 min) with or without cluβ antibody (8 μg/ml) or 1D11 (100 nM). Conditioned medium, obtained from non-treated and TGF-β1-treated BRI-JM01 cells (24 hr), was preincubated (30min) with these antibodies prior to incubation with non-treated BRI-JM01 cells. After 24 hr of exposure, cells were fixed with 4% para-formaldehyde (10 rhin), rinsed twice (PBS), permeabilized (2 min, 0.2% Triton X-100 in PBS), rinsed again, and non-specific sites were blocked with 10% FBS in PBS (40 min). Para-formaldehyde fixed cells were then incubated (1 hr) with primary antibody (E-cad, 1/200; ZO-1, 1/100; cluβ, cav-1; 1/50) in PBS/10% FBS, were rinsed (4× in PBS) and finally were incubated with fluorescently conjugated secondary antibodies (Molecular Probes). Simultaneously, F-actin filaments were labeled with Texas-red labeled phalloidin (1/100) and nuclei were counterstained with 0.4 μg/ml 4,6-diamidino-2-phenylindole (DAPI; Sigma). Slides were rinsed (PBS) and mounted using Prolong anti-fade (Molecular Probes). Fluorescent images were captured using a Princeton Instrument Coolsnap CCD digital camera mounted on Leitz Aristoplan microscope and analyzed using Eclipse (Empix Imaging Inc.) and Photoshop (Adobe) software.

Cell proliferation assays

BRI-JM01 cells ($2.5 \times 10^4$ cells/well) were seeded in 24-well plates. The next day the medium was replenished and purified clusterin, TGF-β1, or TGF-β1 preincubated for 30 min with 1D11 antibody (100 nM) or cluβ antibody (8 μg/ml), was added to the cells. After 24 hr, cells were pulse-labeled with 0.5 μCi/ml [$^3$H]thymidine (Amersham), rinsed (PBS, 4° C.), trypsinized and [$^3$H]thymidine incorporation was evaluated by liquid scintillation counting.

Cell Motility Assays

Cells ($2 \times 10^4$ cells/well) were seeded in ink-coated 12-well plates according to Al-Moustafa et al. (1999) in the absence or presence of TGF-β1, TGF-β1+cluβ antibody, or purified clusterin. Images were captured after 24 hr using a Nikon Coolpix 995 digital camera mounted on Leitz Aristoplan microscope and particle-free tracks were quantified using ImageJ freeware.

Black Ink Motility Assay

Cells ($2 \times 10^4$ cells/well) were seeded in ink-coated 12-well plates according to Al-Moustafa et al. (1999) in the absence or presence of TGF-β1, TGFβ1+cluβ antibody, or purified clusterin. Images were captured after 24 hr using a Nikon Coolpix 995 digital camera mounted on Leitz Aristoplan microscope and particle-free tracks were quantified using ImageJ freeware.

Wound Healing Motility Assay

Confluent cell monolayers (12-well plates) were "wounded" using a 2 μL pipet tip. The medium was then replenished, to remove cell debris, and the anti-clusterin mAbs were added (final concentration of 4 μg/mL) in the absence or presence of 100 pM TGF-β. Images of the wound were captured prior to and after 24 hr of incubation using a Nikon Coolpix 995 digital camera mounted on Leitz Aristoplan microscope.

Polyclonal Antibody Production

The peptide (a.a. 421-437 of the clusterin protein) was produced and purified at the University of Calgary. An extra cysteine was added to the C-terminus of the peptide to facilitate oriented coupling on the surface of the CM-5 sensor chips that were used for screening of the rabbit antisera by surface plasmon resonance (SPR, Biacore.™. 2000). The peptide was coupled to Keyhole Lympet Hemocyanin (KLH, lmject Mariculture KLH; Pierce) using either glutaraldehyde (Sigma) or 1-ethyl-3-(3-dimethylaminopropyl) carbodiimide HCL (Pierce) and dialyzed against PBS (overnight at 4.degree. C.). The peptide preparations that were conjugated by the two methods were mixed (1:1). Pre-immune serum was drawn from two female New Zealand white rabbits (10 ml), which were then injected with the KLH-coupled peptide preparation (1.25 ug peptide per leg/0.5 ml Freund's Incomplete Adjuvant or PBS). Animals were boosted (1.25 ug peptide per leg/0.5 ml Freund's Incomplete Adjuvant or PBS) every third week and serum was drawn (6 ml/kg) every 10 days after each boost until the antibody titer did not increase, at which point the animals were euthanized and exsanguinated.

Sera were tested for antibody activity using SPR. For this, the peptide was coupled to a CM-5 sensor chip (Biacore Inc.) using the Thiol coupling method (as described by the manufacturer) and dilutions (1/50) of the pre-immune sera, the antibody-containing sera and the commercially available anti-clusterin antibody (Santa Cruz) were run over the peptide surface.

Monoclonal Antibody Production

Four BALB/c mice were injected subcutaneously (s.c.) and intra-peritoneally (i.p.) with 35 μg of purified human clusterin emulsified in TiterMax adjuvant (Pierce). Animals were re-injected i.p. three weeks later and the serum titer was assessed 10 days later. Ten weeks later, responsive mice was boosted by i.p. injections (50 μg purified clusterin) and sacrificed three days later. Spleen cells harvested, fused with NS0 myeloma cells and immediately plated ($5 \times 10^4$ cells/well in 96-well microplates; Costar) in Iscove's medium supplemented with 20% FBS, 100 μM hypoxanthine, 0.4 μM aminopterin and 16 μM thymidine (HAT medium), murine IL-6 (1 ng/ml), penicillin (50 U/ml) and streptomycin (50 μg/ml). Supernatants (10-20 days post-fusion) were tested for anti-clusterin activity on immobilized purified clusterin by Enzyme-Linked Immunosorbent Assay (ELISA). Antibody producing cells were cloned and retested twice for anti-clusterin activity. Thirteen anti-clusterin antibody producing clones were generated of which frozen stocks were prepared and a large-scale antibody production was initiated.

SPR-Based Biosensor (Biacore) Epitope Mapping

Approach 1:
  Running buffer:
    HBS (20 mM Hepes (pH7.4), 150 mM NaCl, 3.4 mM EDTA, 0.005% Tween 20)
    All experiments were run at 5 μL/min
  Standard amine coupling of the anti mouse Fc immunoglobulin:
    Inject 35 μL of a mixture of 0.05M NHS and 0.2M EDC
    Inject antibodies diluted in 10 mM NaAc pH5.0 at concentration of 30 μg/mL until an appropriate amount in captured
    Inject 35 μL 1M ethanolamine-HCL pH8.5
  Epitope mapping:
    Inject 25 μL of mAb1 at a concentration of 25 or 50 μg/mL.
    Inject 25 μL of a mixture of IgG1, IgG2a, IgG2b and IgG3 each one at a concentration of 25 μg/mL.
    Inject 25 μL of human recombinant clusterin at a concentration of 30 μg/mL.
    Inject 25 μL of mAb2 at a concentration of 25 or 50 μg/mL.
  Control:
    For each pair of antibodies, the non-specific binding of mab2 was determined by repeating all injections described in the epitope mapping section but injecting running buffer instead of clusterin.
    The response (RU) obtained 20 sec after the end of the mab2 injection in the control was subtracted from the response obtained in the presence of clusterin.
  Regeneration of the surface:
    At the end of each cycle, inject 10 μL of 20 mM glycine pH1.7 followed with 10 μL of 100 mM HCl.

Approach 2:
  Running buffer:
    HBS (20 mM Hepes (pH7.4), 150 mM NaCl, 3.4 mM EDTA, 0.005% Tween 20)
  Standard amine coupling of the antibodies:
    Inject 35 μL of a mixture of 0.05M NHS and 0.2M EDC
    Inject antibodies diluted in 10 mM NaAc (pH4.5 or 5.0) at concentration raging from 20 to 80 μg/mL until a appropriate amount in captured
    Inject 35 μL 1M ethanolamine-HCl pH8.5
  Preparation of control surface
    Inject 35 μL of a mixture of 0.05M NHS and 0.2M EDC
    Inject 35 μL 1M ethanolamine-HCl pH8.5
  Competition
    Mix human recombinant clusterin at 50 nM with 250 nM or 500 nM antibodies in PBS (without Mg++ and Ca++)
    Prepare a tube with antibody alone
    Inject at a flow of 5 μL/min, 25 μL of clusterin alone, antibody alone or clusterin preincubated with antibodies over the antibody and the control surfaces.
    Subtract the response obtained for the antibody alone solution from the response obtained for clusterin preincubated with the same antibody.
    Calculate the % binding inhibition by dividing the response obtained for the clusterin preincubated with antibody by the response obtained for clusterin alone.
  Regeneration solution
    At the end of each cycle, inject 10 mL of 10 mM HCl at a flow rate of 20 μL/min Immunoprecipitation 50 or 100 ng of the various monoclonal antibodies or the polyclonal antibody preparation (C18) was incubated with 20 μL of protein G slush (1:1 in PBS) overnight at 4° C. Then 500 ng of human recombinant clusterin was added and the mixture was incubated for another 2 hr at 4° C. Immunocomplexes were washed 3 times with 1 mL of buffer (150 nM NaCl, 50 mM Tris pH 8.0, 0.55% NP-40, 50 mM Na fluoride) and 20 μL of reducing sample buffer was added. Samples were boiled for 5 min prior to loading on a 12% SDS-PAGE. Separated proteins were then transferred to nitrocellulose and membranes were probed with anti-clusterin antibodies as described.

Sequencing of the monoclonal antibody variable region

Total RNA was isolated from the 12 hybridomas and first strand cDNA was prepared with reverse transcriptase and the Ig-3 constant region primer followed by amplification with the appropriate Ig-5' primer. These primer sets used in conjunction with KOD Hot Start DNA Polymerase specifically amplify the variable regions of light- and heavy-chain cDNAs. PCR products can be directly cloned with Novagen's pSTBlue-1 Perfectly Blunt™ Cloning Kit or treated with the Single dA™ Tailing Kit and cloned into the pSTBlue-1 AccepTor™ Vector. For details see FIG. 13.

TABLE 1

Primer sets used for the validation of some of the 328 TGF-β modulated genes in the BRI-JM01 cells.

| Gene | GeneBank# | Reverse | Forward | size (bp) | |
|---|---|---|---|---|---|
| Eeflal | AW556381 | CTGGCTTCACTGCTCAGGT (SEQ ID NO: 31) | TGGCCAATTGAGACAAACAG (SEQ ID NO: 32) | 457 | Clusterin |
| | AU041878 | TGGTGAAAGCTGTTTGACTCTG (SEQ ID NO: 33) | AAGGCGGCTTTTATTGGATT (SEQ ID NO: 34) | 355 | Integrin α6 |

TABLE 1-continued

Primer sets used for the validation of some of the 328 TGF-β modulated genes in the BRI-JM01 cells.

| Gene | GeneBank# | Reverse | Forward | size (bp) | |
|---|---|---|---|---|---|
| | AW556992 | ATGTGCCATTGTTGCTTTGA (SEQ ID NO: 35) | CAAGCGATGAGCACTTTTGT (SEQ ID NO: 36) | 517 | Caveolin-1 |
| | AU016590 | GTGCAGGAAGGAGAGAATGG (SEQ ID NO: 37) | GCACACCAAGGAGATTGACC (SEQ ID NO: 38) | 247 | |
| Ptpn13 | AW548343 | CCTGCAATGGTTCTTGGTTT (SEQ ID NO: 39) | GGGAAAATCGATGTTGGAGA (SEQ ID NO: 40) | 300 | 14-3-3σ |
| | AA410123 | GGGCTGTTGGCTATCTCGTA (SEQ ID NO: 41) | AGAGACCGAGCTCAGAGGTG (SEQ ID NO: 42) | 297 | |

Inclusion of a reference is neither an admission nor a suggestion that it is relevant to the patentability of anything disclosed herein Bailey et al., Biochemistry. 2001; 40:11828-40
Dunker et al., J Mol Graph Model. 2001; 19 (1):26-59
Li et al., Genome Inform. Ser. Workshop Genome Inform. 1999; 10: 30-
Jones, J. Mol. Biol. 1999; 287: 797-815
Lupas, Meth. in Enzym. 1996; 266: 513-525
Rost, Meth. in Enzym. 1996; 266: 525-539
Singh et al., Curr Opin Drug Discov Devel. 2004: 437-445
Al-Moustafa et al., Biotechniques. 1999: 60-62
Durocher et al Nucleic Acids Res 2002: E9
Enjalbert et al., Mol Biol Cell. 2003: 1460-1467
Schade et al., Mol Biol Cell 2004: 5492-5502
Wilson and Easterbrook-Smith, Biochim Biophys Acta 1992: 319-326

We claim:

1. An isolated antibody which specifically binds to an epitope of clusterin located between amino acids 421 and 443 selected from the group consisting of:
   a) an antibody comprising three complementarity-determining regions of a light chain variable region set forth in SEQ ID NO.:8 and three complementarity-determining regions of a heavy chain variable region set forth in SEQ ID NO.:20;
   b) an antibody comprising three complementarity-determining regions of a light chain variable region set forth in SEQ ID NO.:9 and three complementarity-determining regions of a heavy chain variable region set forth in SEQ ID NO.:20,
   c) an antibody comprising three complementarity-determining regions of a light chain variable region set forth in SEQ ID NO.:10 and three complementarity-determining regions of a heavy chain variable region set forth in SEQ ID NO.:21;
   d) an antibody comprising three complementarity-determining regions of a light chain variable region set forth in SEQ ID NO.11 and three complementarity-determining regions of a heavy chain variable region set forth in SEQ ID NO. :22; and
   e) an antibody comprising three complementarity-determining regions of a light chain variable region set forth in SEQ ID NO.:12 and three complementarity-determining regions of a heavy chain variable region set forth in SEQ ID NO.:23.

2. The antibody of claim 1, wherein said antibody comprises the three complementarity-determining regions of a light chain variable region set forth in SEQ ID NO.:8 and the three complementarity-determining regions of a heavy chain variable region set forth in SEQ ID NO.:20.

3. The antibody of claim 1, wherein said antibody comprises the three complementarity-determining regions of a light chain variable region set forth in SEQ ID NO.:9 and the three complementarity-determining regions of a heavy chain variable region set forth in SEQ ID NO.:20.

4. The antibody of claim 1, wherein said antibody comprises the three complementarity-determining regions of a light chain variable region set forth in SEQ ID NO.:10 and the three complementarity-determining regions of a heavy chain variable region set forth in SEQ ID NO.:21.

5. The antibody of claim 1, wherein said antibody comprises the three complementarity-determining regions of a light chain variable region set forth in SEQ ID NO.:11 and the three complementarity-determining regions of a heavy chain variable region set forth in SEQ ID NO.:22.

6. The antibody of claim 1, wherein said antibody comprises the three complementarity-determining regions of a light chain variable region set forth in SEQ ID NO.: 12 and the three complementarity-determining regions of a heavy chain variable region set forth in SEQ ID NO.:23.

7. A composition comprising the antibody of claim 1 and a pharmaceutically suitable carrier.

8. The antibody or antigen binding fragment of claim 1, wherein said antibody is monoclonal.

9. An isolated antibody which specifically binds to an epitope of clusterin located between amino acids 421 and 443 and which comprises:
   a) a light chain variable region as set forth in SEQ ID NO.: 8 and a heavy chain variable region as set forth in SEQ ID NO.:20;
   b) a light chain variable region as set forth in SEQ ID NO.:9 and a heavy chain variable region as set forth in SEQ ID NO.:20;
   c) a light chain variable region as set forth in SEQ ID NO.: 10 and a heavy chain variable region as set forth in SEQ ID NO.:21;
   d) a light chain variable region as set forth in SEQ ID NO.: 11 and a heavy chain variable region as set forth in SEQ ID NO.: 22, or
   e) a light chain variable region as set forth in SEQ ID NO.: 12 and a heavy chain variable region as set forth in SEQ ID NO.:23.

10. The antibody of claim 9, wherein said antibody comprises a light chain variable region as set forth in SEQ ID NO.: 11 and a heavy chain variable region as set forth in SEQ ID NO.: 22.

11. The antibody of claim 9, wherein said antibody comprises a light chain variable region as set forth in SEQ ID NO.: 12 and a heavy chain variable region as set forth in SEQ ID NO.:23.

12. A composition comprising the antibody of claim 9 and a pharmaceutically suitable carrier.

13. The antibody or antigen binding fragment of claim 9, wherein said antibody is monoclonal.

14. A composition comprising the antibody of claim 10 and a pharmaceutically suitable carrier.

15. The antibody or antigen binding fragment of claim 10, wherein said antibody is monoclonal.

16. A composition comprising the antibody of claim 11 and a pharmaceutically suitable carrier.

17. The antibody or antigen binding fragment of claim 11, wherein said antibody is monoclonal.

18. The composition of claim 7, wherein said antibody is monoclonal.

19. The composition of claim 12, wherein said antibody is monoclonal.

20. The composition of claim 14, wherein said antibody is monoclonal.

21. The composition of claim 16, wherein said antibody is monoclonal.

22. A method for inhibiting epithelial-to-mesenchymal transition in carcinoma cells, the method comprising administering the antibody of claim 1 to a mammal in need.

23. A method for inhibiting epithelial-to-mesenchymal transition in carcinoma cells, the method comprising administering the antibody of claim 9 to a mammal in need.

24. A method for inhibiting epithelial-to-mesenchymal transition in carcinoma cells, the method comprising administering the antibody of claim 10 to a mammal in need.

25. A method for inhibiting epithelial-to-mesenchymal transition in carcinoma cells, the method comprising administering the antibody of claim 11 to a mammal in need.

26. The method of claim 22, wherein said antibody is monoclonal.

27. The method of claim 23, wherein said antibody is monoclonal.

28. The method of claim 24, wherein said antibody is monoclonal.

29. The method of claim 25, wherein said antibody is monoclonal.

* * * * *

SEQUENCE LISTING

```
<160> NUMBER OF SEQ ID NOS: 203

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Glu Val Ser Arg Lys Asn Pro Lys Phe Met Glu Thr Val Ala Glu
1               5                   10                  15

Lys

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Thr Val Ala Glu Lys Ala Leu Gln Glu Tyr Arg
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Thr Val Ala Glu Lys
```

<210> SEQ ID NO 4
<211> LENGTH: 75
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Thr Gln Gly Glu Asp Gln Tyr Tyr Leu Arg Val Thr Thr Val Ala
1               5                   10                  15

Ser His Thr Ser Asp Ser Asp Val Pro Ser Gly Val Thr Glu Val Val
                20                  25                  30

Val Lys Leu Phe Asp Ser Asp Pro Ile Thr Val Thr Val Pro Val Glu
            35                  40                  45

Val Ser Arg Lys Asn Pro Lys Phe Met Glu Thr Val Ala Glu Lys Ala
        50                  55                  60

Leu Gln Glu Tyr Arg Lys Lys His Arg Glu Glu
65                  70                  75

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Glu Val Ser Arg Lys Asn Pro Lys Phe Met Glu Thr Val Ala Glu
1               5                   10                  15

Lys Ala Leu Gln Glu Tyr Arg
                20

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (6)..(6)
<223> OTHER INFORMATION: variable amino acid
<220> FEATURE:
<221> NAME/KEY: MOD_RES
<222> LOCATION: (8)..(8)
<223> OTHER INFORMATION: variable amino acid

<400> SEQUENCE: 6

Gly Tyr Xaa Phe Thr Xaa Tyr Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (2)..(2)
<223> OTHER INFORMATION: Asn or Asp
<220> FEATURE:
<221> NAME/KEY: MOD_RES
<222> LOCATION: (3)..(3)
<223> OTHER INFORMATION: Pro or Thr
<220> FEATURE:
<221> NAME/KEY: MOD_RES
<222> LOCATION: (4)..(4)
<223> OTHER INFORMATION: Tyr or Glu
<220> FEATURE:
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(7)
<223> OTHER INFORMATION: variable amino acid
<220> FEATURE:
<221> NAME/KEY: MOD_RES
<222> LOCATION: (8)..(8)
<223> OTHER INFORMATION: Pro or Thr

<400> SEQUENCE: 7

Ile Xaa Xaa Xaa Xaa Gly Xaa Xaa
1               5

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 8

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      protein
      construct

<400> SEQUENCE: 9

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
```

```
                35                  40                  45
His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Leu Arg
                 85                  90                  95

Thr Phe Gly Gly Gly Thr Lys Leu Glu Ile Lys
            100                 105

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 10

Asp Ile Val Leu Thr Leu Ser Pro Ala Ser Leu Ala Val Ser Leu Gly
 1               5                  10                  15

Gln Arg Ala Thr Ile Ser Cys Arg Ala Ser Gln Ser Val Asn Ser Ser
             20                  25                  30

Asn Tyr Ser Tyr Met His Trp Tyr Gln Gln Lys Pro Gly Gln Pro Pro
         35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr His Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Trp Thr Phe Gly Gly Gly Thr Lys Leu Glu Ile Lys
            100                 105                 110

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 11

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
             20                  25                  30

Ser Asn Gln Lys Asn Tyr Leu Ala Trp Tyr Gln Gln Arg Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ile Tyr Pro Arg Thr Phe Gly Gly Gly Thr Lys Leu Glu Ile
            100                 105                 110

Lys
```

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 12

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Phe Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 13

Asp Val Leu Met Thr Gln Thr Pro Leu Ser Leu Pro Val Ser Pro Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 14

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Ile Pro Arg Thr Phe Gly Gly Gly Thr Lys Leu Glu Ile Lys
            100                 105                 110

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 15

Asp Ile Val Met Thr Gln Ser Pro Ser Ser Leu Ala Met Ser Val Gly
 1               5                  10                  15

Gln Arg Val Thr Met Ser Cys Lys Ser Ser Gln Ser Leu Leu Asn Ser
                20                  25                  30

Asn Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                85                  90                  95

His Tyr Asn Thr Pro Leu Thr Phe Gly Ala Gly Thr Lys Leu Glu Leu
            100                 105                 110

Lys

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 16

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asp Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys

-continued

```
                100             105             110

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 17

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 18

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 19

Glu Ile Val Leu Thr Gln Ser Pro Thr Thr Met Thr Ala Ser Pro Gly
1               5                   10                  15
```

-continued

Glu Lys Ile Thr Ile Thr Cys Ser Ala Ser Ser Ser Ile Ser Ser Asn
            20                  25                  30

Phe Leu His Trp Tyr Gln Gln Lys Pro Gly Phe Ser Pro Lys Leu Leu
        35                  40                  45

Ile Tyr Arg Thr Ser Asn Leu Pro Ser Gly Val Pro Pro Arg Phe Ser
 50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Leu Pro
                85                  90                  95

Arg Thr Phe Gly Ala Gly Thr Lys Leu Ala Leu Lys
            100                 105

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 20

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Thr Pro Asn Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Lys Ser Leu Thr Ser Glu Asp Ser Ala Val Tyr Tyr Cys
            85                  90                  95

Ala Leu Asn Ser Leu Leu Arg Leu Asn Ala Met Asp Tyr Trp Gly Gln
            100                 105                 110

Gly Thr Ser Val Thr Val Ser Ser
        115                 120

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 21

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys

```
                           85                  90                  95
Ala Arg Thr Gly Ser Ser Gly Tyr Phe Asp Cys Trp Gly Gln Gly Thr
                100                 105                 110

Thr Leu Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Gly Phe Leu Tyr Phe Phe Asp Tyr Trp Gly Gln Gly Thr
                100                 105                 110

Thr Leu Thr Val Ser Ser
        115

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 23

Glu Val Gln Leu Gln Gln Ser Gly Ala Glu Leu Val Lys Pro Gly Ala
1               5                   10                  15

Ser Val Arg Leu Ser Cys Thr Thr Ser Gly Phe Asn Ile Lys Asp Ile
            20                  25                  30

Tyr Met His Trp Val Lys Gln Arg Pro Glu Gln Gly Leu Glu Trp Ile
        35                  40                  45

Gly Arg Ile Asp Pro Ala Tyr Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Tyr Asp Thr Ala Met Asp Tyr Trp Gly Gln Gly Thr Ser
                100                 105                 110

Val Thr Val Ser Ser
        115

<210> SEQ ID NO 24
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 24

Glu Val Gln Leu Gln Gln Ser Gly Pro Glu Leu Gly Lys Pro Gly Ala
1               5                   10                  15

Ser Val Lys Ile Ser Cys Lys Ala Ser Gly Tyr Ser Phe Thr Gly Tyr
            20                  25                  30

Asn Met Tyr Trp Val Lys Gln Ser His Arg Lys Ser Leu Glu Trp Ile
        35                  40                  45

Gly Tyr Ile Asp Pro Tyr Asn Gly Asp Thr Ser Tyr Asn Gln Lys Ser
    50                  55                  60

Lys Gly Lys Ala Thr Leu Thr Ala Asp Arg Ser Ser Thr Ala Tyr
65                  70                  75                  80

Met His Leu Asn Ser Leu Thr Ser Glu Asp Ser Gly Ile Tyr Tyr Cys
                85                  90                  95

Ala Arg Gly Ala Tyr Gly Ser Ser Tyr Ala Tyr Trp Gly Gln Gly Thr
            100                 105                 110

Leu Val Ala Val Ser Ala
        115

<210> SEQ ID NO 25
<211> LENGTH: 122
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 25

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Thr Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Thr Arg Ile Tyr Tyr Asp Tyr Gly Ser Trp Asp Gly Phe Ala Tyr Trp
            100                 105                 110

Gly Gln Gly Thr Leu Val Thr Val Ser Ala
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 26

Gln Val Gln Leu Gln Gln Ser Gly Pro Gln Leu Val Arg Pro Gly Ala
```

```
                1               5                   10                  15
Ser Val Lys Ile Ser Cys Lys Ala Ser Asp Tyr Ser Phe Thr Thr Tyr
                20                  25                  30

Trp Met His Trp Val Lys Gln Arg Pro Gly Gln Gly Leu Glu Trp Ile
            35                  40                  45

Gly Met Ile Asp Pro Ser Asp Ser Glu Thr Arg Leu Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ser Arg Asp Gly Asn Tyr Arg Tyr Tyr Thr Leu Asp Phe Trp Gly Gln
            100                 105                 110

Gly Thr Ser Val Thr Val Ser Ser
        115                 120

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 27

Thr Cys Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Thr Ile Ser Thr Ile Gly Ser Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Cys Cys
                85                  90                  95

Thr Arg Glu Asp Tyr Arg Tyr Ala Trp Phe Ala Tyr Trp Gly Gln Gly
            100                 105                 110

Thr Leu Val Thr Val Ser Ala
        115

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 28

Gln Val Gln Leu Gln Gln Ser Gly Pro Gln Leu Val Arg Pro Gly Ala
1               5                   10                  15

Ser Val Lys Ile Ser Cys Lys Ala Ser Asp Tyr Ser Phe Thr Thr Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60
```

-continued

```
Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ser Arg Asp Gly Asn Tyr Arg Ser Tyr Thr Met Asp Tyr Trp Gly Gln
            100                 105                 110

Gly Thr Ser Val Thr Val Ser Ser
        115                 120

<210> SEQ ID NO 29
<211> LENGTH: 115
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 29

Glu Val Gln Leu Val Glu Ser Gly Gly Gly Leu Val Lys Pro Gly Gly
 1               5                  10                  15

Ser Leu Lys Phe Ser Cys Ala Ala Ser Gly Phe Thr Phe Ile Asn Tyr
             20                  25                  30

Ala Met Ser Trp Val Arg Gln Ser Pro Glu Lys Arg Leu Glu Trp Ile
         35                  40                  45

Ala Glu Ile Ser Ser Gly Gly Ser Asp Thr Tyr Tyr Pro Asp Thr Val
     50                  55                  60

Thr Gly Arg Phe Thr Ile Ser Arg Asp Asn Ala Lys Asn Thr Leu Leu
 65                  70                  75                  80

Glu Met Ser Ser Leu Arg Ser Glu Asp Thr Ala Met Tyr Tyr Cys Ala
                 85                  90                  95

Arg Asp Gly Asn Trp Asp Gly Gly Ser Leu Thr Thr Gly Ala Lys Ala
            100                 105                 110

Pro Leu Ser
        115

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 30

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Leu Thr Asp Tyr
             20                  25                  30

Ser Met His Trp Val Lys Gln Ala Pro Gly Lys Gly Leu Lys Trp Met
         35                  40                  45

Gly Trp Ile Asn Thr Glu Thr Gly Glu Pro Thr Tyr Val Asp Asp Phe
     50                  55                  60

Lys Arg Arg Phe Ala Phe Ser Leu Glu Thr Ser Ala Ser Ala Ala Tyr
 65                  70                  75                  80

Leu Gln Ile Asn Asn Leu Lys Asn Glu Asp Thr Ala Thr Tyr Phe Cys
                 85                  90                  95

Thr Arg Asp Gly Ser Ser Thr Phe Ser Tyr Trp Gly Gln Gly Thr
            100                 105                 110
```

Leu Val Thr Val Ser Ala
    115

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctggcttcac tgctcaggt                                                19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggccaattg agacaaacag                                               20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggtgaaagc tgtttgactc tg                                            22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaggcggctt ttattggatt                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgtgccatt gttgctttga                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caagcgatga gcacttttgt                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gtgcaggaag gagagaatgg                                                20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gcacaccaag gagattgacc                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cctgcaatgg ttcttggttt                                                20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gggaaaatcg atgttggaga                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gggctgttgg ctatctcgta                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
agagaccgag ctcagaggtg                                                20

```
<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Tyr Ser Phe Thr Gly Tyr Asn
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Ser Phe Thr Gly Tyr Asn
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Thr Phe Thr Asn Tyr Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Asp Tyr Ser
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Asp Pro Tyr Asn Gly Asp Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

```
Ile Asp Pro Tyr Tyr Gly Thr Pro
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Asn Thr Tyr Thr Gly Glu Pro
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Asn Thr Glu Thr Gly Glu Pro
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Gly Gln Gly Thr Thr Leu Thr Val Ser Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Gly Gln Gly Thr Leu Val Thr Val Ser Ala
1               5                   10

<210> SEQ ID NO 53
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Asn Val Leu Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 54
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 54

Asp Ile Gln Met Thr Gln Ser Pro Ser Ser Leu Ser Ala Ser Leu Gly
1               5                   10                  15

Gly Lys Val Thr Ile Thr Cys Lys Ala Ser
            20                  25

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ile Val Leu Thr Leu Ser Pro Ala Ser Leu Ala Val Ser Leu Gly
1               5                   10                  15

Gln Arg Ala Thr Ile Ser Cys Arg Ala Ser
            20                  25

<210> SEQ ID NO 56
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Ile Val Met Ser Gln Ser Pro Ser Ser Leu Ala Val Ser Ala Gly
1               5                   10                  15

Glu Lys Val Thr Met Ser Cys Lys Ser Ser
            20                  25

<210> SEQ ID NO 57
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Val Leu Met Thr Gln Thr Pro Leu Ser Leu Pro Val Ser Pro Gly
1               5                   10                  15

Asp Gln Ala Ser Ile Ser Cys Arg Ser Ser
            20                  25

<210> SEQ ID NO 58
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Val Val Leu Thr Gln Thr Pro Leu Ser Leu Pro Val Ser Leu Gly
1               5                   10                  15

Asp Gln Ala Ser Ile Ser Cys Arg Ser Ser
            20                  25
```

```
<210> SEQ ID NO 59
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ile Val Met Thr Gln Ser Pro Ser Ser Leu Ala Met Ser Val Gly
1               5                   10                  15

Gln Arg Val Thr Met Ser Cys Lys Ser Ser
            20                  25

<210> SEQ ID NO 60
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Val Val Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Ser Val Ser Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Asp Ile Asn Lys Tyr
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Val Asn Ser Ser Asn Tyr Ser Tyr
1               5                   10

<210> SEQ ID NO 64
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ser Leu Leu Tyr Ser Ser Asn Gln Lys Asn Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Leu Leu Asn Ser Arg Thr Arg Lys Asn Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Ile Val His Ser Asn Gly Asn Thr Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ser Leu Val His Ser Asn Gly Asn Thr Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Ser Leu Leu Asn Ser Asn Asn Gln Lys Asn Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Ser Leu Val His Ser Asn Gly Asp Thr Tyr
1               5                   10
```

```
<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Val Leu Leu Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 71
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ile Val Met Thr Gln Ser Pro Ala Thr Leu Ser Val Thr Pro Gly
1               5                   10                  15

Asp Arg Val Ser Leu Ser Cys Arg Ala Ser
            20                  25

<210> SEQ ID NO 72
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Ile Val Leu Thr Gln Ser Pro Thr Thr Met Thr Ala Ser Pro Gly
1               5                   10                  15

Glu Lys Ile Thr Ile Thr Cys Ser Ala Ser
            20                  25

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Leu Val His Ser Asn Gly Asn Thr Tyr
1               5                   10

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ser Ile Ser Asp Tyr
1               5
```

```
<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ser Ile Ser Ser Asn Phe
1               5

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Val Gln Leu Gln Gln Ser Gly Pro Glu Leu Glu Lys Pro Gly Ala
1               5                   10                  15

Ser Val Lys Ile Ser Cys Lys Ala Ser
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Val Gln Leu Gln Gln Ser Gly Ala Glu Leu Val Lys Pro Gly Ala
1               5                   10                  15

Ser Val Arg Leu Ser Cys Thr Thr Ser
```

```
<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Val Gln Leu Gln Gln Ser Gly Pro Glu Leu Gly Lys Pro Gly Ala
1               5                   10                  15

Ser Val Lys Ile Ser Cys Lys Ala Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Val Gln Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Val Gln Leu Gln Gln Ser Gly Pro Gln Leu Val Arg Pro Gly Ala
1               5                   10                  15

Ser Val Lys Ile Ser Cys Lys Ala Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Cys Lys Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84
```

Gln Val Gln Leu Gln Gln Ser Gly Pro Gln Leu Val Arg Pro Gly Ala
1               5                   10                  15

Ser Val Lys Ile Ser Cys Lys Ala Ser
            20                  25

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Tyr Ser Phe Thr Gly Tyr Asn
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Tyr Thr Phe Thr Asp Tyr Ser
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Thr Phe Thr Asn Tyr Gly
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Phe Asn Ile Lys Asp Ile Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Tyr Ser Phe Thr Gly Tyr Asn
1               5

<210> SEQ ID NO 90
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Phe Thr Phe Ser Ser Tyr Ala
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Tyr Ser Phe Thr Thr Tyr Trp
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Phe Thr Phe Ser Ser Tyr Ser
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Tyr Ser Phe Thr Thr Tyr Trp
1               5

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Val Gln Leu Val Glu Ser Gly Gly Gly Leu Val Lys Pro Gly Gly
1               5                   10                  15

Ser Leu Lys Phe Ser Cys Ala Ala Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95
```

```
Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Phe Thr Phe Ile Asn Tyr Ala
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Tyr Thr Leu Thr Asp Tyr Ser
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met His Trp Tyr Gln Gln Lys Ser Ser Thr Ser Pro Lys Leu Trp Ile
1               5                   10                  15

Tyr

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Ala Trp Tyr Gln His Lys Pro Gly Lys Gly Pro Arg Leu Leu Ile
1               5                   10                  15

His

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met His Trp Tyr Gln Gln Lys Pro Gly Gln Pro Pro Lys Leu Leu Ile
1               5                   10                  15
```

Lys

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Ala Trp Tyr Gln Gln Arg Pro Gly Gln Ser Pro Lys Leu Leu Ile
1               5                   10                  15

Tyr

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Ala Trp Tyr Gln Gln Lys Pro Gly Gln Ser Pro Lys Leu Leu Ile
1               5                   10                  15

Tyr

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Glu Trp Tyr Leu Gln Lys Pro Gly Gln Ser Pro Lys Leu Leu Ile
1               5                   10                  15

Tyr

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu His Trp Tyr Leu Gln Lys Pro Gly Gln Ser Pro Lys Leu Leu Ile
1               5                   10                  15

Tyr

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Ala Trp Tyr Gln Gln Lys Pro Gly Gln Ser Pro Lys Leu Leu Val
1               5                   10                  15

Tyr

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu His Trp Tyr Leu Gln Lys Pro Gly Gln Ser Pro Lys Leu Leu Ile
1               5                   10                  15

Tyr

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu His Trp Tyr Leu Gln Lys Pro Gly Gln Ser Pro Lys Leu Leu Ile
1               5                   10                  15

Tyr

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu His Trp Tyr Gln Gln Lys Ser His Glu Ser Pro Arg Leu Leu Ile
1               5                   10                  15

Lys

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu His Trp Tyr Gln Gln Lys Pro Gly Phe Ser Pro Lys Leu Leu Ile
1               5                   10                  15

Tyr

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Met Asn Trp Val Lys Gln Asn Asn Gly Lys Ser Leu Glu Trp Ile Gly
1               5                   10                  15

Asn

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Met His Trp Val Lys Gln Ala Pro Gly Lys Gly Leu Lys Trp Met Gly
1               5                   10                  15

Trp

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met His Trp Val Lys Gln Ala Pro Gly Lys Gly Leu Lys Trp Met Gly
1               5                   10                  15

Trp

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Met His Trp Val Lys Gln Arg Pro Glu Gln Gly Leu Glu Trp Ile Gly
1               5                   10                  15

Arg

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Met Tyr Trp Val Lys Gln Ser His Arg Lys Ser Leu Glu Trp Ile Gly
1               5                   10                  15

Tyr

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Met Ser Trp Val Arg Gln Ser Pro Glu Lys Arg Leu Glu Trp Val Ala
1               5                   10                  15

Glu

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met His Trp Val Lys Gln Arg Pro Gly Gln Gly Leu Glu Trp Ile Gly
1               5                   10                  15

Met

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Ser Trp Val Arg Gln Thr Pro Glu Lys Arg Leu Glu Trp Val Ala
1               5                   10                  15

Thr

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Met His Trp Val Lys Gln Arg Pro Gly Gln Gly Leu Glu Trp Ile Gly
1               5                   10                  15

Met

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Asp Pro Tyr Tyr Gly Thr Pro
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Asn Thr Glu Thr Gly Glu Pro
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Asn Thr Tyr Thr Gly Glu Pro
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Asp Pro Ala Tyr Gly Asn Thr
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Asp Pro Tyr Asn Gly Asp Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Ser Ser Gly Gly Thr Tyr Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ile Asp Pro Ser Asp Ser Glu Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Ile Ser Thr Ile Gly Ser Tyr Thr
1               5
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Ile Asp Pro Ser Asp Ser Glu Thr
1               5
```

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Met Ser Trp Val Arg Gln Ser Pro Glu Lys Arg Leu Glu Trp Ile Ala
1               5                   10                  15
Glu
```

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Met His Trp Val Lys Gln Ala Pro Gly Lys Gly Leu Lys Trp Met Gly
1               5                   10                  15
Trp
```

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Ile Ser Ser Gly Gly Ser Asp Thr
1               5
```

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Ile Asn Thr Glu Thr Gly Glu Pro
1               5
```

<210> SEQ ID NO 132
<211> LENGTH: 36

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Leu Ala Ser Gly Val Pro Gly Arg Phe Ser Gly Ser Gly Ser Gly
1               5                   10                  15

Asn Ser Tyr Ser Leu Thr Ile Ser Ser Met Glu Ala Glu Asp Val Ala
            20                  25                  30

Thr Tyr Tyr Cys
        35

<210> SEQ ID NO 133
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Leu Gln Pro Gly Ile Pro Ser Arg Phe Ser Gly Ser Gly Ser Gly
1               5                   10                  15

Arg Asp Tyr Ser Phe Ser Ile Ser Asn Leu Glu Pro Glu Asp Ile Ala
            20                  25                  30

Thr Tyr Tyr Cys
        35

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asn Leu Glu Ser Gly Val Pro Ala Arg Phe Ser Gly Ser Gly Ser Gly
1               5                   10                  15

Thr His Phe Thr Leu Asn Ile His Pro Val Glu Glu Glu Asp Thr Ala
            20                  25                  30

Thr Tyr Tyr Cys
        35

<210> SEQ ID NO 135
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Arg Glu Ser Gly Val Pro Asp Arg Phe Thr Gly Ser Gly Ser Gly
1               5                   10                  15

Thr Asp Phe Thr Leu Thr Ile Ser Ser Val Lys Ala Glu Asp Leu Ala
            20                  25                  30

Val Tyr Tyr Cys
        35

<210> SEQ ID NO 136
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Arg Glu Ser Gly Val Pro Asp Arg Phe Thr Gly Ser Gly Ser Gly
1               5                   10                  15

Thr Asp Phe Thr Leu Thr Ile Ser Ser Val Gln Ala Glu Asp Leu Ala
            20                  25                  30

Val Tyr Tyr Cys
        35

<210> SEQ ID NO 137
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 138
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Arg Glu Ser Gly Val Pro Asp Arg Phe Ile Gly Ser Gly Ser Gly
1               5                   10                  15

Thr Asp Phe Thr Leu Thr Ile Ser Ser Val Gln Ala Glu Asp Leu Ala
            20                  25                  30

Asp Tyr Phe Cys
        35

<210> SEQ ID NO 140
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Gln Gly Ser Gly Tyr Pro Phe Thr
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Gln Tyr Asp Asn Leu Leu Arg Thr
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln His Ser Trp Glu Ile Pro Trp Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Tyr Tyr Ile Tyr Pro Arg Thr
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 145

Lys Gln Ser Tyr Asn Leu Trp Thr
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Phe Gln Gly Ser His Val Pro Tyr Thr
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Gln Ser Thr His Ile Pro Arg Thr
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Gln His Tyr Asn Thr Pro Leu Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Gln Ser Thr His Val Pro Arg Thr
1               5

<210> SEQ ID NO 150
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Arg Phe Ser Gly Val Pro Asp Arg Phe Ser Gly Ser Gly Ser Gly
1               5                   10                  15

Thr Asp Phe Thr Leu Asn Ile Ser Arg Val Glu Ala Glu Asp Leu Gly
                20                  25                  30

```
Val Tyr Phe Cys
        35

<210> SEQ ID NO 151
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Ser Ile Ser Gly Ile Pro Ser Arg Phe Ser Gly Ser Gly Ser Gly
1               5                   10                  15

Ser Asp Phe Thr Leu Ser Ile Asn Ser Val Glu Pro Glu Asp Val Gly
            20                  25                  30

Val Tyr Tyr Cys
        35

<210> SEQ ID NO 152
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Leu Pro Ser Gly Val Pro Pro Arg Phe Ser Gly Ser Gly Ser Gly
1               5                   10                  15

Thr Ser Tyr Ser Leu Thr Ile Gly Thr Met Glu Ala Glu Asp Val Ala
            20                  25                  30

Thr Tyr Tyr Cys
        35

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Gln Ser Thr His Val Pro Arg Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Asn Gly His Ser Phe Pro Tyr Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 155

Gln Gln Gly Ser Ser Leu Pro Arg Thr
1               5

<210> SEQ ID NO 156
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Tyr Asn Gln Lys Phe Lys Gly Lys Ala Thr Leu Thr Val Asp Lys
1               5                   10                  15

Ser Ser Ser Thr Ala Tyr Met Gln Leu Lys Ser Leu Thr Ser Glu Asp
            20                  25                  30

Ser Ala Val Tyr Tyr Cys
        35

<210> SEQ ID NO 157
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Thr Tyr Ala Asp Asp Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe Cys
        35

<210> SEQ ID NO 158
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Tyr Ala Asp Asp Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe Cys
        35

<210> SEQ ID NO 159
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Tyr Asp Pro Lys Phe Gln Gly Lys Ala Thr Ile Thr Ala Asp Thr
1               5                   10                  15

Ser Ser Asn Thr Ala Tyr Leu Gln Leu Ser Ser Leu Thr Ser Glu Asp
```

Thr Ala Val Tyr Tyr Cys
        35

<210> SEQ ID NO 160
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Tyr Asn Gln Lys Ser Lys Gly Lys Ala Thr Leu Thr Ala Asp Arg
1               5                   10                  15

Ser Ser Ser Thr Ala Tyr Met His Leu Asn Ser Leu Thr Ser Glu Asp
            20                  25                  30

Ser Gly Ile Tyr Tyr Cys
        35

<210> SEQ ID NO 161
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Tyr Tyr Pro Asp Thr Val Thr Gly Arg Phe Thr Ile Ser Arg Asp Asn
1               5                   10                  15

Ala Lys Asn Thr Leu Tyr Leu Glu Met Ser Ser Leu Arg Ser Glu Asp
            20                  25                  30

Thr Ala Met Tyr Tyr Cys
        35

<210> SEQ ID NO 162
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Leu Asn Gln Lys Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
            20                  25                  30

Ser Ala Val Tyr Tyr Cys
        35

<210> SEQ ID NO 163
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Tyr Pro Asp Ser Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp

```
                    20                  25                  30

Thr Ala Met Tyr Cys Cys
        35

<210> SEQ ID NO 164
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Leu Asn Gln Lys Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
            20                  25                  30

Ser Ala Val Tyr Tyr Cys
        35

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Leu Asn Ser Leu Leu Arg Leu Asn Ala Met Asp Tyr
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Arg Thr Gly Ser Ser Gly Tyr Phe Asp Cys
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Arg Asp Gly Phe Leu Tyr Phe Phe Asp Tyr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Arg Arg Tyr Asp Thr Ala Met Asp Tyr
1               5                   10
```

```
<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Arg Gly Ala Tyr Gly Ser Ser Tyr Ala Tyr
1               5                   10

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Arg Ile Tyr Tyr Asp Tyr Gly Ser Trp Asp Gly Phe Ala Tyr
1               5                   10                  15

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Arg Asp Gly Asn Tyr Arg Tyr Tyr Thr Leu Asp Phe
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Arg Glu Asp Tyr Arg Tyr Ala Trp Phe Ala Tyr
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Arg Asp Gly Asn Tyr Arg Ser Tyr Thr Met Asp Tyr
1               5                   10

<210> SEQ ID NO 174
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 174

Tyr Tyr Pro Asp Thr Val Thr Gly Arg Phe Thr Ile Ser Arg Asp Asn
1               5                   10                  15

Ala Lys Asn Thr Leu Leu Glu Met Ser Ser Leu Arg Ser Glu Asp Thr
            20                  25                  30

Ala Met Tyr Tyr Cys
            35

<210> SEQ ID NO 175
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Thr Tyr Val Asp Asp Phe Lys Arg Arg Phe Ala Phe Ser Leu Glu Thr
1               5                   10                  15

Ser Ala Ser Ala Ala Tyr Leu Gln Ile Asn Asn Leu Lys Asn Glu Asp
            20                  25                  30

Thr Ala Thr Tyr Phe Cys
            35

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Arg Asp Gly Asn Trp Asp Gly Gly Ser Leu Thr
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Thr Arg Asp Gly Ser Ser Thr Trp Phe Ser Tyr
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Ser Gly Thr Lys Leu Glu Ile Lys
1               5

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Phe Gly Gly Gly Thr Lys Leu Glu Ile Lys
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Phe Gly Gly Gly Thr Lys Leu Glu Ile Lys
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Phe Gly Gly Gly Thr Lys Leu Glu Ile Lys
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Phe Gly Gly Gly Thr Lys Leu Glu Phe Lys
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Phe Gly Gly Gly Thr Lys Leu Glu Ile Lys
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Phe Gly Gly Gly Thr Lys Leu Glu Ile Lys
1               5                   10

<210> SEQ ID NO 185
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Gly Ala Gly Thr Lys Leu Glu Leu Lys
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Phe Gly Gly Gly Thr Lys Leu Glu Ile Lys
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Phe Gly Gly Gly Thr Lys Leu Glu Ile Lys
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Phe Gly Gly Gly Thr Lys Leu Glu Ile Lys
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Phe Gly Ala Gly Thr Lys Leu Ala Leu Lys
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Trp Gly Gln Gly Thr Ser Val Thr Val Ser Ser
1               5                   10
```

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Gly Gln Gly Thr Thr Leu Thr Val Ser Ser
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Trp Gly Gln Gly Thr Thr Leu Thr Val Ser Ser
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Trp Gly Gln Gly Thr Ser Val Thr Val Ser Ser
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Gly Gln Gly Thr Leu Val Ala Val Ser Ala
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Gly Gln Gly Thr Leu Val Thr Val Ser Ala
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 196

Trp Gly Gln Gly Thr Ser Val Thr Val Ser Ser
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Trp Gly Gln Gly Thr Leu Val Thr Val Ser Ala
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Trp Gly Gln Gly Thr Ser Val Thr Val Ser Ser
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Ala Lys Ala Pro Leu Ser Gln Ser Pro Gln
1               5                   10

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Trp Thr Thr Gly Val Lys Glu Pro Gln Ser Pro Ser Pro Gln
1               5                   10                  15

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Leu Gly Pro Arg Asp Ser Gly Arg Cys Leu Cys
1               5                   10

<210> SEQ ID NO 202
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 202

Ile Leu Trp Thr Thr Gly Val Lys Glu Pro Gln Ser Pro Ser Pro Gln
1               5                   10                  15

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Thr Thr Gly Ala Lys Ala Pro Leu Ser Gln Ser Pro Gln
1               5                   10
```